(12) United States Patent
Van Holten et al.

(10) Patent No.: US 7,655,233 B2
(45) Date of Patent: Feb. 2, 2010

(54) OPTIMAL PLACEMENT OF A ROBUST SOLVENT/DETERGENT PROCESS POST VIRAL ULTRAFILTRATION OF AN IMMUNE GAMMA GLOBULIN

(75) Inventors: Robert W. Van Holten, Flemington, NJ (US); Stephen M. Autenrieth, Bernardsville, NJ (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 264 days.

(21) Appl. No.: 11/274,812

(22) Filed: Nov. 15, 2005

(65) Prior Publication Data

US 2006/0110399 A1    May 25, 2006

(51) Int. Cl.
    *A61K 39/00*    (2006.01)
(52) U.S. Cl. .................................................. 424/176.1
(58) Field of Classification Search ........................ None
    See application file for complete search history.

(56) References Cited

U.S. PATENT DOCUMENTS

| | | | |
|---|---|---|---|
| 2,390,074 | A | 12/1945 | Cohn |
| 3,449,314 | A | 6/1969 | Pollack |
| 3,686,395 | A | 8/1972 | Stephan |
| 3,916,026 | A | 10/1975 | Stephan |
| 3,962,421 | A | 6/1976 | Neurath |
| 4,021,540 | A | 5/1977 | Pollack et al. |
| 4,141,887 | A | 2/1979 | Seufert |
| 4,540,573 | A | 9/1985 | Neurath et al. |
| 4,590,002 | A | 5/1986 | Zolton et al. |
| 4,764,369 | A | 8/1988 | Neurath et al. |
| 4,859,340 | A | 8/1989 | Hou et al. |
| 4,880,913 | A | 11/1989 | Doleschel et al. |
| 5,094,960 | A | 3/1992 | Bonomo |
| 5,110,910 | A | 5/1992 | Tsav |
| 5,115,101 | A | 5/1992 | Bloom |
| 5,132,406 | A | 7/1992 | Uemura et al. |
| 5,215,681 | A | 6/1993 | Truong et al. |
| 5,288,853 | A | 2/1994 | Bhattacharya et al. |
| 5,486,293 | A | 1/1996 | Boschetti et al. |
| 5,609,763 | A | 3/1997 | Boschetti et al. |
| 5,723,123 | A | 3/1998 | Karges et al. |
| 5,733,885 | A | 3/1998 | Eibl et al. |
| 5,817,765 | A | 10/1998 | Isaksson et al. |
| 5,858,641 | A | 1/1999 | Shanbrom |
| 5,945,098 | A | 8/1999 | Sarno et al. |
| 6,096,872 | A | 8/2000 | Van Holten et al. |
| 6,124,437 | A | 9/2000 | Hirao et al. |
| 6,166,187 | A | 12/2000 | Prusiner et al. |
| 6,221,614 | B1 | 4/2001 | Prusiner et al. |
| 6,270,672 | B1 | 8/2001 | Turecek et al. |
| 6,369,048 | B1 | 4/2002 | Budowsky et al. |
| 6,468,733 | B2 | 10/2002 | Nur et al. |
| 2002/0009707 | A1* | 1/2002 | Nur et al. .................... 435/2 |
| 2002/0018777 | A1 | 2/2002 | Prince et al. |
| 2002/0151688 | A1 | 10/2002 | Ristol Debart et al. |
| 2004/0033224 | A1 | 2/2004 | Van Holten et al. |
| 2004/0110931 | A1 | 6/2004 | Van Holten |

FOREIGN PATENT DOCUMENTS

| | | |
|---|---|---|
| EP | 1161958 | 12/2001 |
| WO | WO 96/00237 A1 | 1/1996 |
| WO | WO 98/08603 A1 | 3/1998 |
| WO | WO 99/19343 A1 | 4/1999 |
| WO | WO 00/43048 A1 | 7/2007 |

OTHER PUBLICATIONS

Shaked, Gideon M., et al., "A Protease-Resistant Prion Protein Isoform Is Present in Urine of Animals and Humans Affected with Prion Diseases", J. Biol. Chem., 2001, 276(34), 31479-31482.

Prusiner, Stanley B., et al., "Molecular Properties, Partial Purification, and Assay by Incubation Period Measurements of the Hamster Scrapie Agent", Biochemistry, 1980, 19, 4883-4891.

Winklhofer, Konstanze F., et al., "A Sensitive Filter Retention Assay for the Detection of $PrP^{Sc}$ and the Screening of Anti-Prion Compounds", FEBS Letters 2001, 503: 41-45.

Wadsworth, J.D.F., et al., "Tissue Distribution of Protease Resistant Prion Protein in Variant Creutzfeldt-Jakob Disease Using a Highly Sensitive Immunoblotting Assay", Lancet, 2001, 358: 171-180.

Safar, Jiri, et al., "Eight Prion Strains Have $PrP^{Sc}$ Molecules With Different Conformations", Nature Medicine, 1998, 4(10): 1157-1165.

MacGregor, I, "Prion Protein and Developments In Its Detection", Transfusion Medicine, 2001, 11: 3-14.

Pocchiari, Maurizio, et al., "Combination Ultrafiltration and 6 $M$ Urea Treatment of Human Growth Hormone Effectively Minimizes Risk From Potential Creutzfeldt-Jakob Disease Virus Contamination", Horm. Res, 1991, 35: 161-166.

Gölker, C. F., et al., Reduction of the Infectivity of Scrapie Agent as a Model for BSE in the Manufacturing Process of Trasylol®, Biologicals, 1996, 24: 103-111.

Saborio, Gabriela P., et al., "Sensitive Detection of Pathological Prion Protein by Cyclic Amplification of Protein Misfolding", Nature, 2001, 411: 810-813.

Prowse, C. V., "Preliminary Assessment of Whole-Blood, Red-Cell and Platelet-Leucodepleting Filters for Possible Induction of Prion Release By Leucocyte Fragmentation During Room Temperature Processing", British Journal of Haematology, 1999, 106: 240-247.

"EMEA Expert Workshop on Human TSEs and Plasma-Derived Medicinal Products", The European Agency for the Evaluation of Medicinal Products *Evaluation of Medicines for Human Use*, CPMP/BWP/1244/00, 1-13, London, 2000.

(Continued)

*Primary Examiner*—Sandra E Saucier

(57) ABSTRACT

The solvent-detergent (S/D) process is used to inactivate enveloped viruses in plasma products. While concentrations of 1.0% detergent and 0.3% tri-n-butyl phosphate solvent have been considered necessary for robust removal of viral activity, we show the effectiveness of solvent-detergent treatment after fractionation and nanofiltration of an immune gamma globulin preparation, which required significantly reduced concentrations of solvent and detergent. Reduced levels of solvent and detergent lead to greater efficiencies in their removal post-inactivation with the potential for greater yields and decreased processing costs.

9 Claims, 11 Drawing Sheets

OTHER PUBLICATIONS

Van Holten, Robert W., et al., "Incorporation of an additional viral-clearance step into a human immunoglobulin manufacturing process". Vox Sang 2002; 83:227-233.

Van Holten, Robert W., et al., "Removal of Prion Challenge From an Immune Globulin Preparation By Use of a Size-Exclusion Filter", Transfusion, 2002, 42: 999-1004.

Van Holten, Robert et al., "Evaluation of Depth Filtration to Remove Prion Challenge From an Immune Globulin Preparation", Vox Sang, 2003, 85: 20-24.

Turner, M.L., et al., "New-Variant Creutzfeldt-Jakob Disease: The Risk of Transmission by Blood Transfusion", Blood Reviews, 1998, 12:255-268, Churchill Livingstone, Edinburgh.

Burnouf, T., Value of Virus Filtration as a Method for Improving the Safety of Plasma Products, Vox Sang, 1996, 70:235-236.

Burnouf, T.. et al., "Reducing the Risk of Infection from Plasma Products: Specific Preventative Strategies", Blood Reviews, 2000, 14:94-110, Harcourt Publishers Ltd.

Burnouf, T. et al., "Nanofiltration of plasma-derived biopharmaceutical products". Haemophilia 2003; 9; 24-37.

Foster, P.R., "Assessment of the Potential of Plasma Fractionation Processes to Remove Causative Agents of Transmissible Spongiform Encephalopathy", Transfusion Medicine, 1999, 9:3-14.

Foster, P.R., et al., "Studies on the Removal of Abnormal Prior Protein by Processes Used in the Manufacture of Human Plasma Products", Vox Sang, 2000, 78:86-95.

Lee, Douglas C., et al., "Monitoring Plasma Processing Steps With a Sensitive Western Blot Assay for the Detection of the Prion Protein", JVMEDH, 2000, 84(1), 77-89.

Lee, Douglas C., et al., "A Direct Relationship Between the Partitioning of the Pathogenic Priom Protein and the Transmissible Spongiform Encephalopathy Infectivity During the Purification of Plasma Proteins", Transfusion, 2001, 41(4), 449-455.

Cohn, E.J., et al., "Preparation and Properties of Serum and Plasma Proteins. IV. A System for the Separation into Frantions of the Protein and Lipoprotein Components of Biological Tissues and Fluids", J. Am Chem. Soc., 1946, 68, 459-475.

Arky, R., "Ortho Diagnostic Systems, Inc.", Physicians' Desk Reference MICRhoGAM™, Medical Economics Data Production Co. Montvale, NJ. pp. 1770-1771, Apr. 1995.

Roberts, Peter L., "Value to Virus Filtration as a Method for Improving the Safety of Plasma Products", Vox Sang, S. Kargar AG, Basel, CH, vol. 69, No. 1, pp. 82-83, Jul. 1995.

Roberts, Peter L., "Effect of manufacturing process parameters on virus inactivation by solvent-detergent treatment in a high-purity factor IX concentrate", Vox Sang 2003; 84:170-175.

DiLeo, Anthony J., et al., "Size Exclusion Removal of Model Mammalian Viruses Using a Unique Membrane System, Part 1: Membrane Qualification", Biologicals (1993) 21:275-286.

Tateishi, Jun, et al., "Removal of Causative Agent of Cruetzfeldt-Jakob Disease (CJD) Through Membrane Filtration Method", (Original Contribution) (Membrane), 18(6), 357-362 (1993).

Bridonneau, P., et al., "Liquid Pasteurization of an Immunoglobulin Preparation with Stabilizer: Effects on its Biological and Biochemical Properties", Vox Sang 1996;70:203-209.

Hardy, R.R., "Purification and Characterization of Monoclonal Antibodies", Handbook of Experimental Immunology in Four Volumes. D.M. Weir, Editor. Blackwell Scientific Publications. Oxford. pp. 13.1-13.13.

Troccoli. Noreen M., et al., "Removal of Viruses from Human Intravenous Immune Globulin by 35 nm Nanofiltration", Biologicals (1998) 26, 321-329.

Horowitz B., et al., "Inactivation of Viruses in Labile Blood Derivatives". I. Disruption of Lipid-enveloped Viruses by Tri(n-butyl)phosphate Detergent Combinations. Transfusion 1985; 25(6):516-22.

Horowitz B., et al., "Virus Inactivation by Solvent/detergent Treatment and the Manufacture of SD-plasma". Vox Sang 1998; 74, Suppl. 1:203-206.

Horowitz B., et al., Solvent/Detergent-Treated Plasma: A Virus-Inactivated Substitute for Fresh Frozen Plasma, Blood 1992; 79(3):826-831.

Uemura Y., et al., "Inactivation and Elimination of Viruses During Preparation of Human Intravenous Immunoglobulin". Vox Sang 1994; 67(3):246-254.

Product Insert for SDR HyperD Solvent-Detergent Removal Sorbent, Ciphergen Biosystems, Inc., Fremont CA 94555, P/N 290053, Rev. Jul. 2002.

Guerrier, L., et al., "Specific Sorbent to Remove Solvent-Detergent Mixtures from Virus-Inactivated Biological Fluids". J. Chromatogr B, 664 (1995), 119-125.

Biesert L., et al., "Solvent/Detergent Treatment of Human Plasma—A Very Robust Method for Virus Inactivation. Validated Virus Safety of OCTAPLAS®", Vox Sang 1998, 74, Suppl. 1:207-212.

Biesert L., "Virus validation studies of immunoglobulin preparations", Clin. Exp. Rheumatol 1996, 14, Suppl. 15:547-52.

Murozuka, T., et al., "Removal and Inactivation of Hepatitis B Virus from Contaminated Pooled Plasma in a Large-Scale Manufacturing Process for Factor VIII and Human Serum Albumin". Vox Sang 1999; 76:181-186.

Edwards, C.A., et al., "Tri(n-Butyl) Phosphate/Detergent Treatment of Licensed Therapeutic and Experimental Blood Derivatives", Vox Sang 1987; 52:53-59.

Trescec, A., et al., "Removal of detergent and solvent from solvent-detergent-treated immunoglobulins". J. Chromatogr A. 1999; 852(1):87-91.

Josic D., et al., "Purification of factor VIII and von Willebrand factor from human plasma by anion-exchange chromatography". J. Chromatogr B 1994; 662(2):181-190.

Josic D., et al., "Issues in the development of medical products based on human plasma[1]". J. Chromatogr B 1997; 694:253-269.

Milwidsky, A., "A Rapid Method for the Production Control of the Non-ionic Component in Synthetic Detergents", Analyst 1969; 94:377-386.

Karlsson, G., et al., "Determination of Triton X-100 in plasma-derived coagulation factor VIII and factor IX products by reversed-phase high-performance liquid chromatography". J Chromatogr A 2002; Feb 8; 946(1-2):163-168.

Nellaiappan, K., et al., "Validation of a simple and sensitive gas chromatographic method for the analysis of tri-η-butyl phosphate from virally inactivated human immunoglobulin". J. Chromatogr B Biomed Sci Appl.; 2001; Jun. 5; 757(1):181-189.

Piet, M.P.J., et al., "The use of tri(n-butyl)phosphate detergent mixtures to inactivate hepatitis viruses and human immunodeficiency virus in plasma and plasma's subsequent fractionation". Transfusion 1990: 30:591-598.

Hilfenhause, J. et al., "Analysis of human plasma products: polymerase chain reaction does not discriminate between live and inactivated viruses". Transfusion, vol. 37, Sep. 1997, pp. 935-940.

Griffith, M., "Ultrapure plasma factor VIII produced by anti-F VIII c immunoaffinity chromatography and solvent/detergent viral inactivation. Characterization of the Method M process and Hemofil M antihemophilic factor (human)". Ann Hematol 1991; 63. 131-137.

Gebauer B., et al., "Ion-exchange chromatography separation of the detergent and the solvent from immunoglobulins after solvent-detergent treatment", J. Chromatogr A 1999; 852:83-86.

Seitz, H., et al., "Comparable Virus Inactivation by Bovine or Vegetable Derived Tween 80 During Solvent/Detergent Treatment". Biologicals 2002; 30:197-205.

Biggerstaff, et al., "Estimated risk of West Nile virus transmission through blood transfusion during an epidemic in Queens, New York City". Transfusion 42, Aug. 2002 pp. 1019-1026.

Remington, K.M., et al., "Inactivation of West Nile cirus, vaccinia virus and viral surrogates for relevant and emergent viral pathogens in plasma-derived products". Vox Sang Jul. 2004; 87(1) 10-18.

CPMP Note for Guidance on Virus Validation: The Design, Contribution and Interpretation of Studies Validating the Inactivation and Removal of Viruses. CPMP/BWP/268/95 Final Version 2 (1996).

CPMP Note for Guidance on Plasma-Derived Medical Products. CPMP/Biotechnology Working Party (BWP) 269/95, Rev. 2 (1996).

European Search Report dated Jan. 16, 2004, for European Appln. No. 02 25 2375.

PCT International Search Report dated Sep. 3, 2004, for PCT Int'l Appln. No. PCT/US03/16347.

European Search Report, dated Feb. 20, 2006, for European Appln. No. EP 05257095.

Prusiner, Stanley B., "Transmissible Spongiform Encephalopathies—Impact on Animal and Human Health", "Prion Encephalopathies of Animals and Humans", Developments in Biological Standardization, Basel Karger, 1993, pp. 31-34, vol. 80.

Van Holten, R. W., et al., "Incorporation of Viral Clearance Step into a Modified Cohen Fractionation", Transfusion, Abstract Supplement, Oct. 1995, pp. S52, 13 Supplement, vol. 35.

Oncley, J.L., et al., "The Separation of the Antibodies, Isoagglutinins, Prothrombin, Plasminogen and $\beta_1$-Lipoprotein into Subfractions of Human Plasma", J. Am. Chem Soc., Feb. 1949, pp. 541-550, vol. 71.

Tomasi, Thomas B., Immunobiology, Current Knowledge of Basic Concepts in Immunology and their Clinical Applications, The Gamma A Globulins: First Line of Defense, 1971, pp. 76-83, Chapter 8.

Dorland's Illustrated Medical Dictionary, Title page, Definition of Immunoglobulin, W.B. Saunders Co., Philadelphia, 1994, pp. 823-825, 28th Edition.

* cited by examiner

FIG. 6

Solvent/Detergent Treatment of WNV Spiked RhoGAM

Legend:
- 1X S/D
- 0.1X S/D
- 0.05X S/D
- 0.02X S/D
- 0.01X S/D
- 0.005X S/D

X-axis: Time (minutes)
Y-axis: Viral Load ($\text{Log}_{10}\ \text{TCID}_{50}$)

OPTIMAL PLACEMENT OF A ROBUST SOLVENT/DETERGENT PROCESS POST VIRAL ULTRAFILTRATION OF AN IMMUNE GAMMA GLOBULIN

BACKGROUND OF THE INVENTION

This invention relates to the field of viral inactivation of blood products and blood product compositions, including blood, blood components, blood plasma or any fraction, concentrate or derivative thereof containing blood proteins, plasma-containing products and plasma fraction-containing products containing labile proteins, for example immunoglobulins, through use of a solvent/detergent process to accomplish same. In particular the solvents used include the di- and tri-alkyl phosphates and the detergents include partial esters of sorbital anhydrides, including oxyethylated alkylphenols and in particular the Tritons®. The blood products are thereby rendered substantially free of enveloped viruses such as for example the hepatitis viruses and other viral infectivity, such blood products and blood product compositions are thus purified.

The solvent-detergent (S/D) process has been in use for close to 20 years to inactivate enveloped viruses in plasma products; it continues to be the viral inactivation method by which other novel methods are compared. Concentrations of 1.0% detergent and 0.3% tri-n-butyl phosphate (TNBP) solvent have been considered necessary for robust removal of viral activity. The S/D treatment generally requires more chemicals and takes a longer time to perform when accomplished at the front end of the process (where the process volumes are greater and the product less well defined, as a result of raw material being typically of less purity and potency) than later in the process, when impurities have been reduced and the product is in most cases better defined and of greater purity and potency with reduced volume, or where viral load has been reduced or diminished by at least one robust viral removal step (i.e., resulting in a log removal of $\geq/=4$ logs for enveloped virus and $\geq/=3$ logs for non-enveloped virus).

This invention discloses the effectiveness of solvent-detergent treatment after fractionation and nanofiltration or size exclusion filtration of a blood product or blood product composition for example such as an immune gamma globulin preparation, allowing use of significantly reduced concentrations of solvent and detergent. This invention further discloses the surprising finding that when used after size exclusion filtration in a purified protein system, 10 to 20 times less S/D chemicals are required to accomplish complete inactivation of enveloped virus as compared to S/D viral inactivation concentrations used by fractionators and experts trained in the art over the last 20 years.

A preferred method of the instant invention discloses removal of the S/D chemicals. In accordance therewith, it is disclosed that the S/D chemicals can be effectively removed by using a diffusion column containing silica beads in which the pore volume is filled with a three-dimensional cross-linked hydrophobic acrylic polymer to reduce protein binding to the silica. Such column is specifically designed for removal of S/D from a well-defined protein solution. By practicing the solvent/detergent process at the reduced concentrations discussed herein it becomes feasible to require 10 to 20 times less column material to rid the product of solvent/detergent post the viral inactivation treatment. Such small packing makes it feasible in most cases to dispose of the chromatographical material post each use. This is important to control possible cross contamination between batches due to the presence of live non-enveloped virus and prion particles associated with TSEs.

The S/D process has continued to be the more favorable viral inactivation approach to blood product purification; other more invasive and destructive techniques include use of aldehydes and ultraviolet light have proved too denaturing or destructive of the protein. Aside from blood products and blood product compositions, any protein solution having the possibility of viral contamination can be purified using the methods of the invention. For example, protein-containing solutions comprising mammalian milk, ascites fluid, saliva, placental extracts, tissue culture extracts, products of fermentation, transgenic derived products and recombinant proteins can all be purified by these methods. In Applicants' methods the preferred protein solutions for purification are blood products and blood product compositions.

In one embodiment of this invention, there is disclosed (1) a method for post-manufacture S/D treatment of human or animal derived proteins after size exclusion filtration of the protein; (2) a method for such S/D treatment that therefore uses much less solvent and detergent than previously used in the industry; and (3) means for removing the S/D by using silica beads in which the pore volume is filled with a three-dimensional cross-linked hydrophobic acrylic polymer to reduce protein binding to the silica. The use of the latter material allows the removal of detergent and reduces the endotoxin load in the product. The beads use the silica's natural ability to capture S/D while the polymer allows for greater than 95% recovery of the protein of interest, e.g. IgG.

It is disclosed herein the kinetics of viral inactivation in a protein as a post manufacturing step, specifically, in a purified immunoglobulin after fractionation and nanofiltration. We determined the amount of solvent and detergent could be reduced and still maintain a robust viral inactivation. The ability to decrease the amount of TNBP and Triton X-100 could reduce the amount of material required to remove the S/D to the point where it would be economically feasible to simply discard the sorbent, eliminating the need to regenerate the material. This would eliminate the requirement to validate sorbent regeneration, and minimize concerns about breakthrough of the S/D chemicals or extractables leaching from the material after repeated use.

In a preferred embodiment of the invention, the viral inactivation methods are performed on the human immune gamma globulin known commercially as RhoGAM® Ultra Filtered. (Ortho-Clinical Diagnostics, Inc., Raritan N.J.) Rho (D) Immune Globulin (Human) was the first successful prophylactic use of specific antibody to achieve antibody mediated immune suppression. RhoGAM® is an IgG immunoglobulin solution containing anti-Rho(D) at a dose of 300 micrograms of anti-D activity per dose. RhoGAM® can be given to the nonimmunized, Rho(D) negative pregnant woman at the appropriate time prevent future disease in her Rho(D) positive offspring. The disease is called hemolytic disease of the newborn or more specifically, Rh-erythroblastosis fetalis.

A smaller dose of anti-Rho(D), MICRhoGAM® Rho(D) Immune Globulin (Human) Micro-Dose (50 micrograms of anti-Rho(D)) is also sold by the Assignee hereof for treatment of women who have abortions and miscarriages at twelve weeks gestation or earlier. While the full dose protects the recipient for up to 15 ml of Rho(D) positive red cells, the smaller dose provides protection up to 2.5 ml of Rho(D) positive red cells. RhoGAM® is used as antenatal prophylaxis at 26 to 28 weeks gestation. Other indications include threatened abortion at any stage of gestation with continuation of pregnancy, abortion or termination of pregnancy at or beyond 13 weeks gestation, abdominal trauma or genetic amniocentesis, chorionic villus sampling (CVS) and percutaneous umbilical blood sampling (PUBS).

Most immunoglobulin injectable materials approved for use by the FDA and Bureau of Biologics have been produced by the alcohol fractionation procedure developed by Dr. E. Cohn of Harvard during the 1940s and described in Cohn et al., J. Am. Chem. Soc. 68, 459 (1946), incorporated herein by reference. This procedure, coupled with the careful selection of plasma negative for hepatitis infectivity, HIV, and other blood-borne pathogens determined by the most sensitive tests available, has insured that the resultant preparation of this procedure as safe. This fact can easily be demonstrated by the millions of non-infected recipients of product.

According to the current RhoGAM® Ultra Filtered manufacturing process, anti-D-containing plasma is fractionated (See Cohn et al., supra) and the resulting precipitate is resuspended in buffer and virally cleared using the Viresolve™ ultra-filtration membrane. The virally-cleared material is diafiltered and concentrated using a Biomax size exclusion filter. Protein concentration and pH are adjusted and the resulting bulk material is filled into syringes. See commonly-assigned U.S. Pat. No. 6,096,872.

Solvent/detergent treatment is widely accepted as a method for inactivating lipid-enveloped viruses in plasma and plasma-derived therapeutic proteins. Numerous studies have demonstrated the effectiveness of this process with plasma, immunoglobulin preparations, coagulation factor concentrates and other plasma proteins.

Typically, when performing a solvent/detergent treatment, solvent and detergent are added to plasma at the start (front end) of a manufacturing process at concentrations of 1% each, or at an intermediate step in processing at concentrations of 0.3% and 1.0% respectively. The instant invention discloses a unique viral inactivation step in that lower concentrations of solvent (ranging from about 0.003%-less than 0.3% TNBP) and detergent (ranging from about 0.01% to less than 1.0% Triton X-100) are used, post manufacture, to inactivate virally-cleared, lipid-free bulk product. The removal process for eliminating solvent and detergent from the final product is also unique in that it is accomplished without an extraction step. Instead solvent and detergent are removed directly by use of a silica bead sorbent material. While the sorbent material can be regenerated, it is preferred that the sorbent material will be for one-time use only.

As herein disclosed it is preferable to add a virus-inactivation step post manufacture of the current RhoGAM® Ultra Filtered process. The prior art has considered concentrations of 1.0% detergent and 0.3% tri-n-butyl phosphate (TNBP) solvent necessary for robust removal of viral activity. In contrast to these high concentrations of S/D, using the methods of the instant invention, human Immune gamma globulin (RhoGAM®) bulk material can be treated post manufacture with about 0.01%-less than 1.0% detergent (such as Triton X-100) and about 0.003% to less than 0.3% solvent (such as Tri (n-butyl) phosphate (TNBP)). The treatment in a preferred embodiment is for a minimum of about 1 hour at 15° C.-25° C. The above ranges for solvent and detergent will be expected to vary with variations in temperature and/or extended times of incubation; for instance, increased temperatures and/or extended incubation times will allow for even lower S/D concentrations. After treatment, solvent and detergent are preferably removed by passage of material through a column containing a silica sorbent material, for example, SDR Hyper D Solvent-Detergent Removal sorbent (manufactured by the BioSepra Division of Ciphergen Biosystems, Inc., Fremont, Calif.). The sorbent is composed of silica beads in which the pore volume is filled with a three dimensional cross-linked hydrophobic polymer that retains solvent and detergent. Virus inactivated RhoGAM® (RhoGAM SD™) is collected, diafiltered and concentrated using a Biomax filter. Polysorbate 80 concentration, pH and protein concentration may then be adjusted such that the final RhoGAM SD™ product is consistent with the current formulation.

The S/D step may also be employed at the front end of the manufacture process. Where the S/D step is employed in the inventive process at the front end of the manufacture, it is preferable to employ about 0.2% to less than 1.0% solvent and about 0.2% to less than 1.0% detergent.

A flow chart of the proposed manufacturing steps required for viral inactivation is provided in FIG. 1

SUMMARY OF THE INVENTION

The present invention provides a method for viral inactivation of a blood product, using significantly reduced concentrations of solvent and detergent, wherein the solvent/detergent step is preferably employed post-manufacture of the product. The method of the invention results in a preparation of substantially virus-free sterile blood product or composition having an extent of inactivation of lipid-coated virus greater than 4 logs of said virus and wherein the yield of blood product protein is at least 90%.

The method includes virally purifying a blood product comprising contacting said blood product post-manufacture with at least one solvent in the concentration range of about 0.003% to less than 0.3% and at least one detergent in the concentration of about 0.01% to less than 1.0% wherein the method results in the extent of inactivation of lipid-coated virus greater than 4 logs of said virus and wherein the yield of blood product protein is at least 90%. In preferred embodiments, the concentration of solvent is in the range of about 0.006% to less than 0.3%, more preferably from about 0.015% to about 0.15%, more preferably from about 0.03% to about 0.15%, and most preferably from about 0.03% to about 0.06% and most preferably about 0.06%. In preferred embodiments, the concentration of detergent is in the range of about 0.02% to less than 1.0%, more preferably from about 0.05% to about 0.5%, more preferably from about 0.1% to about 0.5%, more preferably from about 0.1% to about 0.2% and most preferably about 0.2%.

In the preferred methods of the instant invention, the solvent-detergent step is performed after the size exclusion filtration, however it may also be performed at the front end of the manufacture process. When the S/D method is performed at the front end of the process, the solvent is preferably used at about 0.2% to less than 1.0% and the detergent in the concentration of about 0.2% to less than 1.0%.

For the purposes of the invention, the blood product or composition can be for example, protein-containing solutions comprising mammalian milk, ascites fluid, saliva, placental extracts, tissue culture extracts, products of fermentation, transgenic derived products and recombinant proteins, monoclonal or polyclonal IgG, or coagulation products.

In another embodiment there is disclosed a post-manufacturing method of substantially virally purifying a human immune globulin comprising contacting said finished product of human immune globulin with at least one organic solvent at least one detergent wherein the method results in the extent of inactivation of lipid-coated virus greater than 4 logs of said virus and wherein the amount of blood product protein is at least 90% and wherein the solvent detergent is removed using diffusion sorbent. The sorbent material can be introduced to the product by running the solvent/detergent product through a column packed with the sorbent or the sorbent can be directly introduced into the product and later removed by either centrifugation or by exclusion filtration, or decanting. When using diffusion chromatography, a preferred embodiment is to run the product through a sorbent column.

The present invention is directed inter alia, to producing a blood product composition such as blood, blood plasma and blood fractions, etc., which are substantially free of virions yet which contains a substantial amount of blood product protein. More particularly, the invention is directed inactivation of lipid-containing virus and preferentially inactivation of such virus as hepatitis B and C virus. Other viruses inactivated by the instant method include for example, cytomegalovirus, Epstein-Barr virus, herpes group virus, and paramyxovirus.

In particular, in the methods of the instant invention, such blood product is preferably a human immune gamma globulin fractionated in accordance with a full-scale modified Cohn-Oncley cold alcohol fractionation scheme as disclosed in Cohn et al., supra and in co-assigned U.S. Pat. No. 6,096,872, followed by nanofiltration using a Viresolve 180 size-exclusion filter (RhoGAM® Ultra-Filtered $Rh_o(D)$ Immune Globulin (Human), Ortho-Clinical Diagnostics, Raritan, N.J.). This nanofiltration was performed in accordance with the methods of co-assigned U.S. Pat. No. 6,096,872.

Purification of such blood products can also take place by tangential filtration, ion exchange chromatography, affinity chromatography or electrophoretic means or a combination of these techniques.

BRIEF DESCRIPTION OF THE DRAWING

FIGS. 1A, 1B and 1C designate the Product Holding Tank, as 1, the Viral Clearance Filter Holder as 2, the Ultrafiltration Filter Holder as 3, the 50 mM NaCl-Glycine Buffer Storage Tank as 4, the T-1 Recirculation Tank as 5, the T-2 UF Recirculation Tank as 6, the P1 Viresolve 180 Feed Pump as 7, the Viresolve 180 Permeate Pumps as 8, the UV Meter as 9, the UF Feed Pump as 10, the UF Permeate as 11, the Sample Port as 12, and the Product Recovery and In-Line Sterile Filtration as 13.

FIG. 6 is a graph showing viral inactivation using the S/D treatment methods of the present invention on WNV spiked IgG. See Example 2 herein.

DETAILED DESCRIPTION

Figure 1:
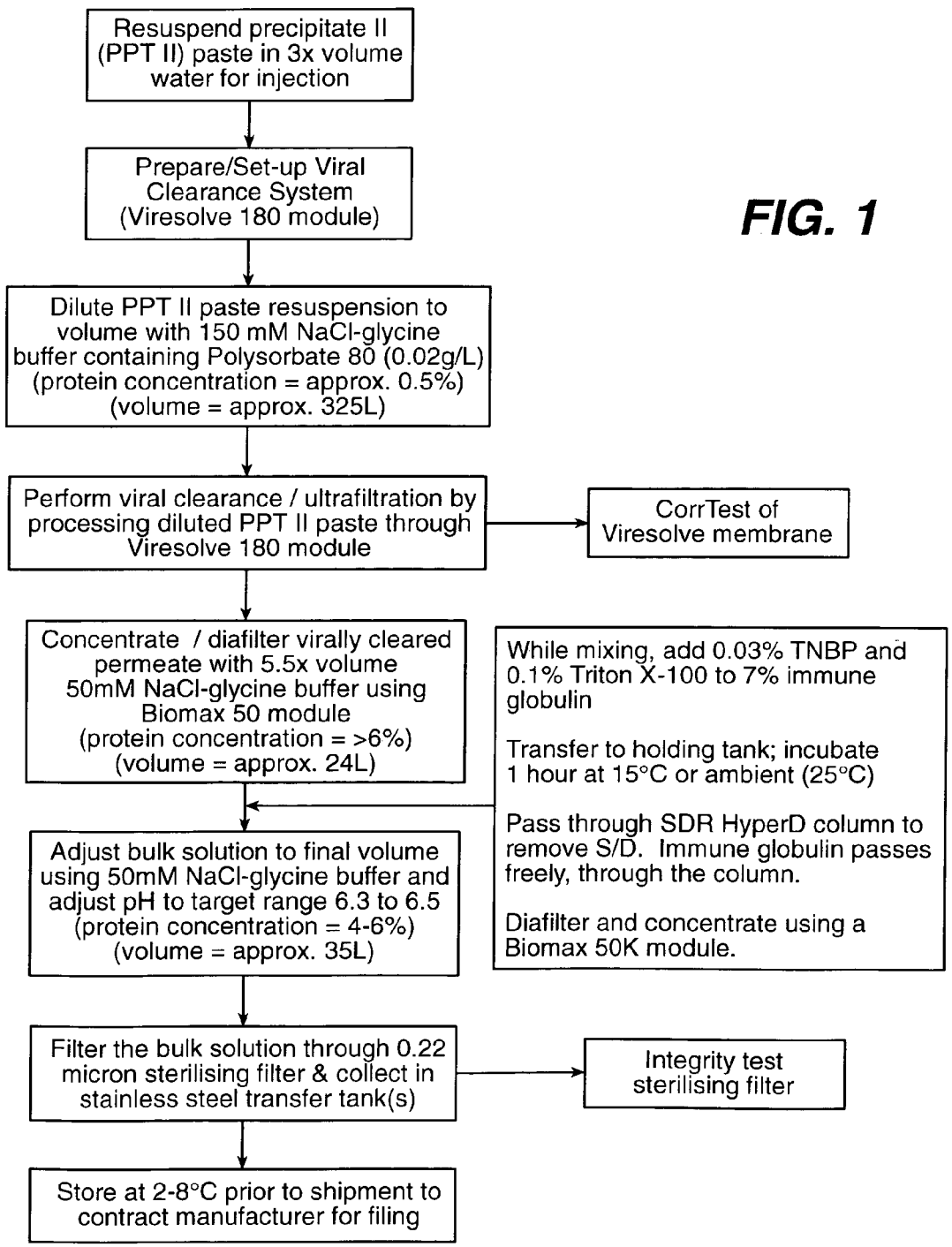
FIG. 1 is a flowchart of the RhoGAM® solvent detergent viral inactivation process.
Figure 1A:
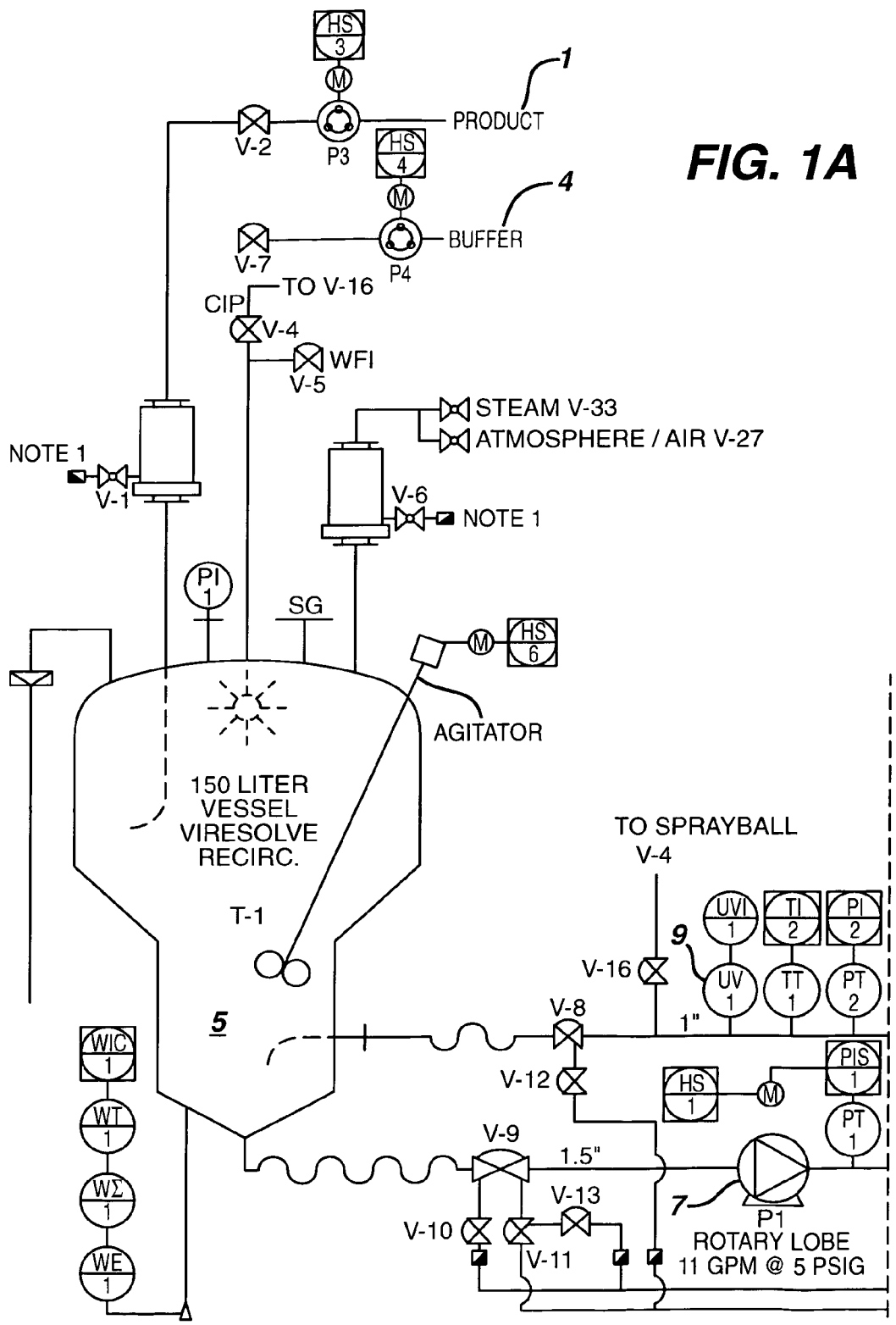
FIGS. 1A, 1B and 1C are schematic drawings showing the VIRESOLVE® 180 SYSTEM Ultrafiltration System used in the prion- and viral-clearance process of the invention.
Figure 1B:
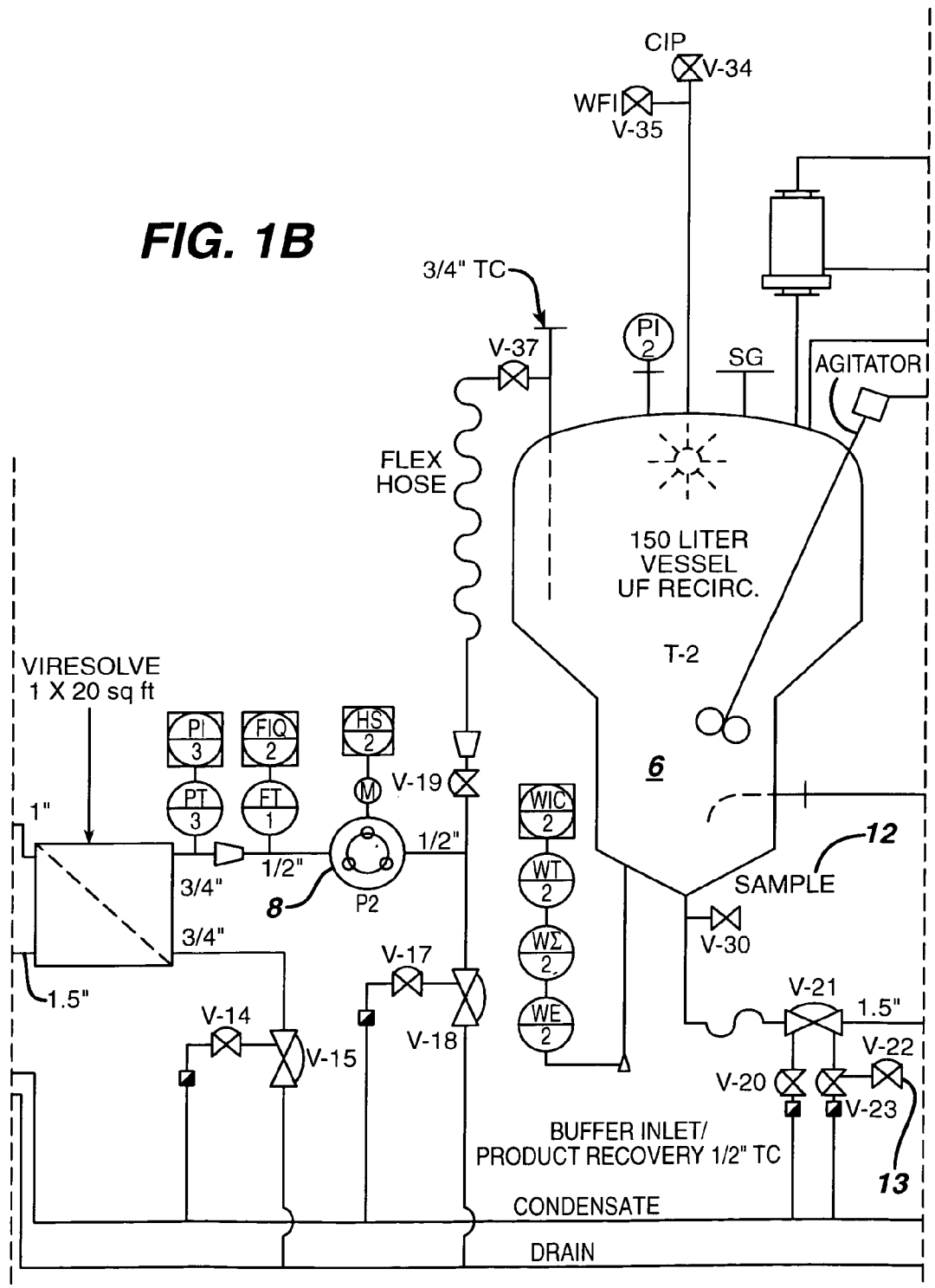
Figure 1C:
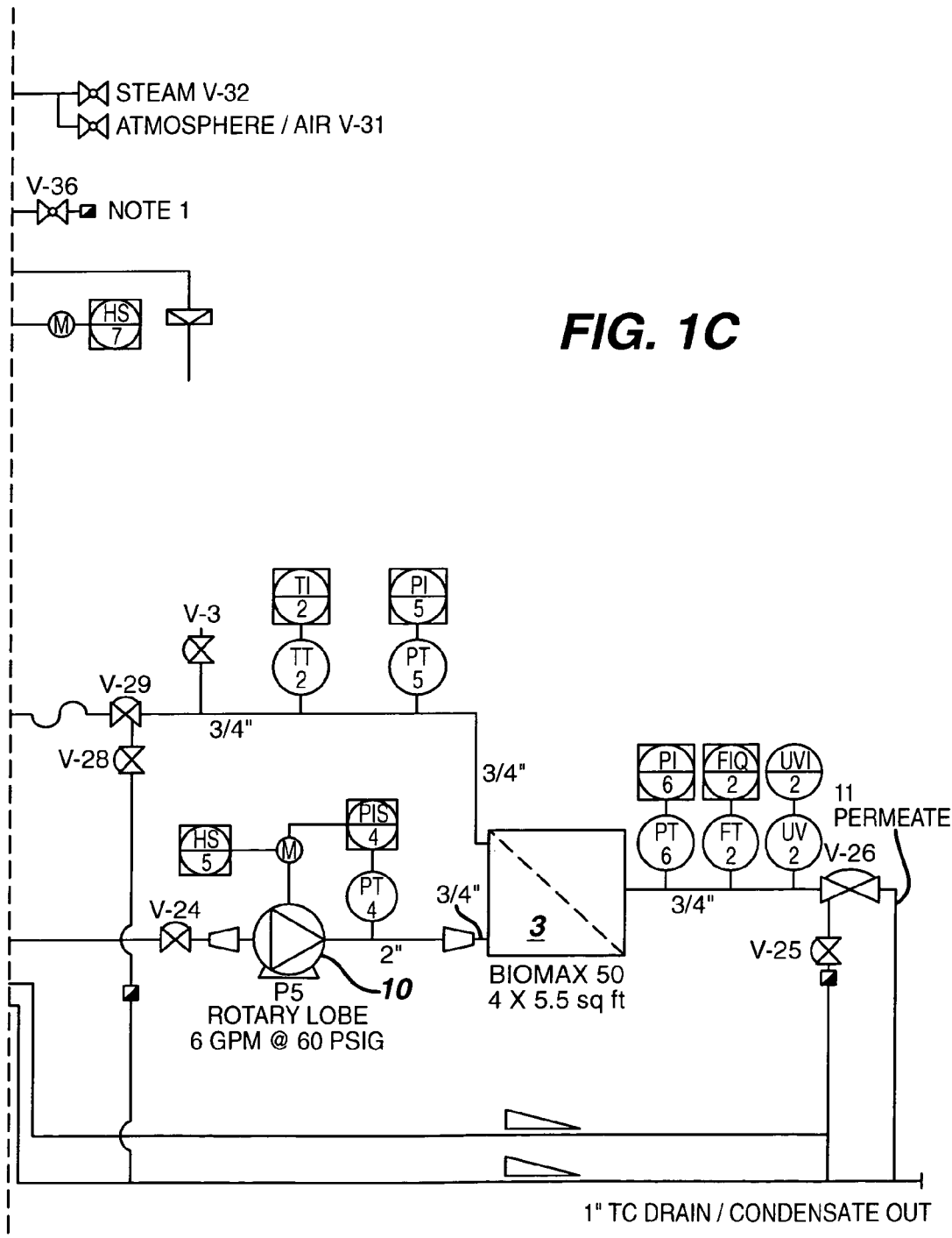

This invention describes a method for viral inactivation of a protein composition, for example a blood product or blood product composition as a post-manufacturing step for example following size exclusion filtration of the blood product or blood product composition, using significantly reduced concentrations of solvent and detergent than in prior art methods. In one purified protein system, after size exclusion filtration, 10 to 20 times less S/D chemicals are required to completely inactivate enveloped viruses in said purified blood product as compared to the prior art methods. Such a purified protein system is a blood product, and more particularly, is purified human immune gamma globulin or the RhoGAM® Ultra-Filtered and MICRhoGAM® Ultrafiltered products (Ortho-Clinical Diagnostics, Inc., Raritan, N.J.).

RhoGAM® Ultra-Filtered is a sterile solution containing human anti-D immunoglobulin. It is a parenteral product used to prevent Rh(D) immunization in Rh(D) negative individuals exposed to Rh(D) positive red blood cells. The preparation is intended for intramuscular administration. It is obtained from the plasma of Rh(D) negative donors who either have antibody from a previous transfusion or pregnancy, or who have been immunized against the D antigen. A smaller dose of anti-Rho(D), MICRhoGAM® Rho(D) Immune Globulin (Human) Micro-Dose (50 micrograms of anti-Rho(D)) is also sold by the Assignee hereof for treatment of women who have abortions and miscarriages at twelve weeks gestation or earlier. While the full dose protects the recipient for up to 15 ml of Rho(D) positive red cells, the smaller dose provides protection up to 2.5 ml of Rho(D) positive red cells.

Protein-containing compositions including solutions can be purified using the methods of the instant invention. For example, those compositions that can be purified include blood products and blood product compositions, including for example, whole blood, blood plasma or any fraction, concentrate or derivative thereof containing blood proteins, plasma concentrates, blood components, plasma-containing products and plasma fraction-containing products containing labile proteins, for example immunoglobulins, a precipitate from a plasma fractionation, a supernatant from fractionation of plasma, serum, a cryoprecipitate, a cryosupernatant, a cell lysate and proteins induced in blood cells including monoclonal and polyclonal antibodies. Other proteins that can be purified using these methods include mammalian milk, ascites fluid, saliva, placental extracts, tissue culture extracts including transformed cell extracts, products of fermentation transgenic derived products and recombinant proteins.

The method of the present invention permits the treatment of pooled blood product compositions. Such blood product can then be used as is or further processes as desired, as a substantially virus purified composition.

The present invention is directed inter alia, to producing a blood product composition such as blood, blood plasma and blood fractions, etc., which are substantially free of virions yet which contains a substantial amount of blood product protein. More particularly, the invention is directed inactivation of lipid-containing virus and preferentially inactivation of such virus as hepatitis B and C virus.

The method is herein described in terms of treatment of liquid blood components such as plasma and plasma fractions however it is also useful in treating solid components of blood, lysates or proteins thereof such as concentrates, and like solid compositions and blood components, etc. According to the methods of the invention one can treat plasma itself or fresh frozen plasma or thawed frozen plasma, cryoprecipitate, cryosupernatant or concentrates from frozen plasma as well as dilution products thereof. Such preparations may be treated using the methods of this invention either at the front end of manufacture or post manufacture.

In particular, such blood product is preferably a human immune gamma globulin fractionated in accordance with a full-scale modified Cohn-Oncley cold alcohol fractionation scheme as disclosed in Cohn et al., supra and in co-assigned U.S. Pat. No. 6,096,872, followed by nanofiltration using a Viresolve 180 size-exclusion filter (RhoGAM® Ultra-Filtered Rho(D) Immune Globulin (Human), Ortho-Clinical Diagnostics, Raritan, N.J.). This nanofiltration was performed in accordance with the methods of co-assigned U.S. Pat. No. 6,096,872. This material was stored under sterile conditions at 2-8° C. until use.

Figure 2:
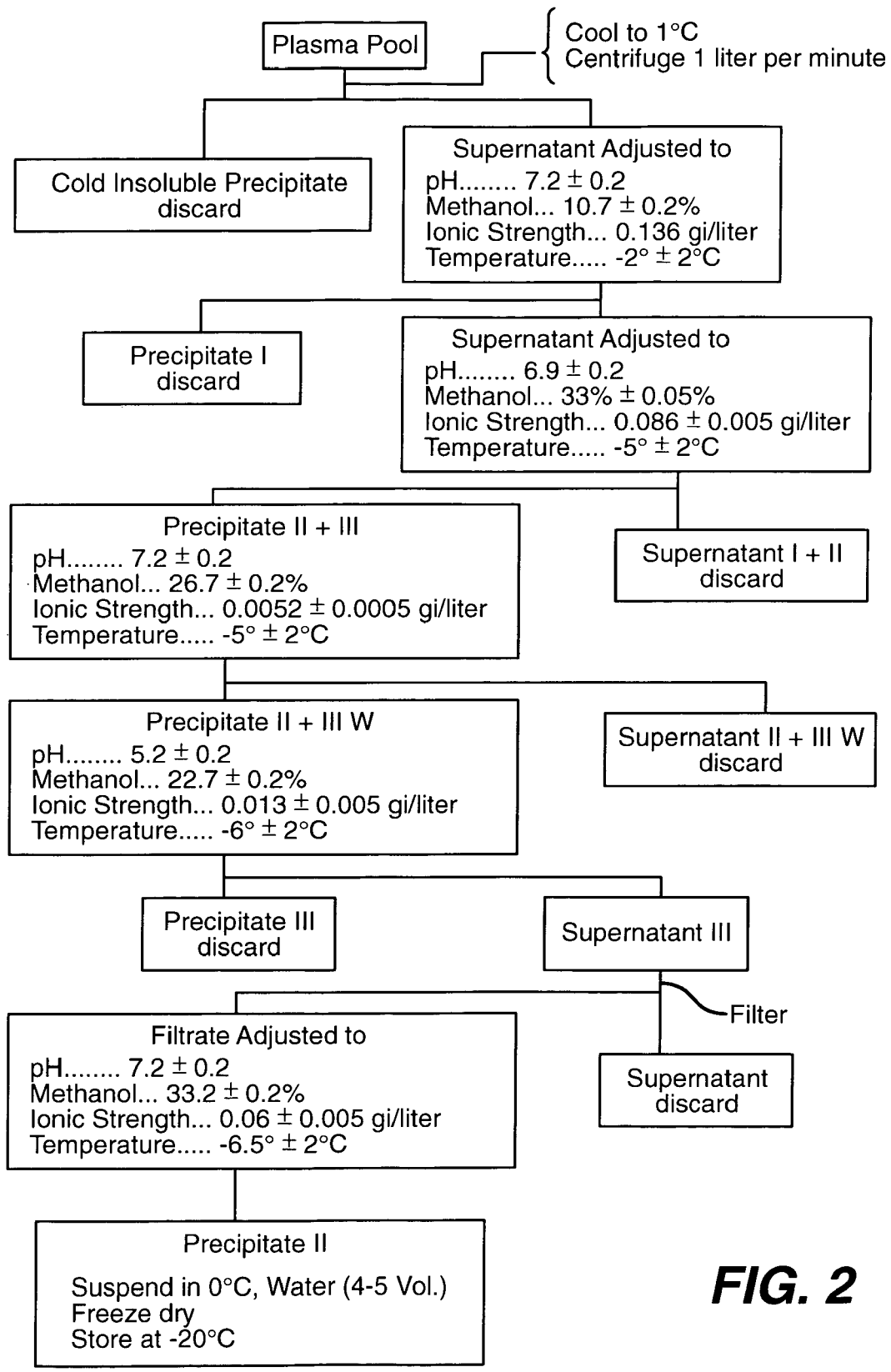
FIG. 2 is a flow sheet showing the process of fractionation of human plasma to obtain anti-Rh globulin.
Figure 3:
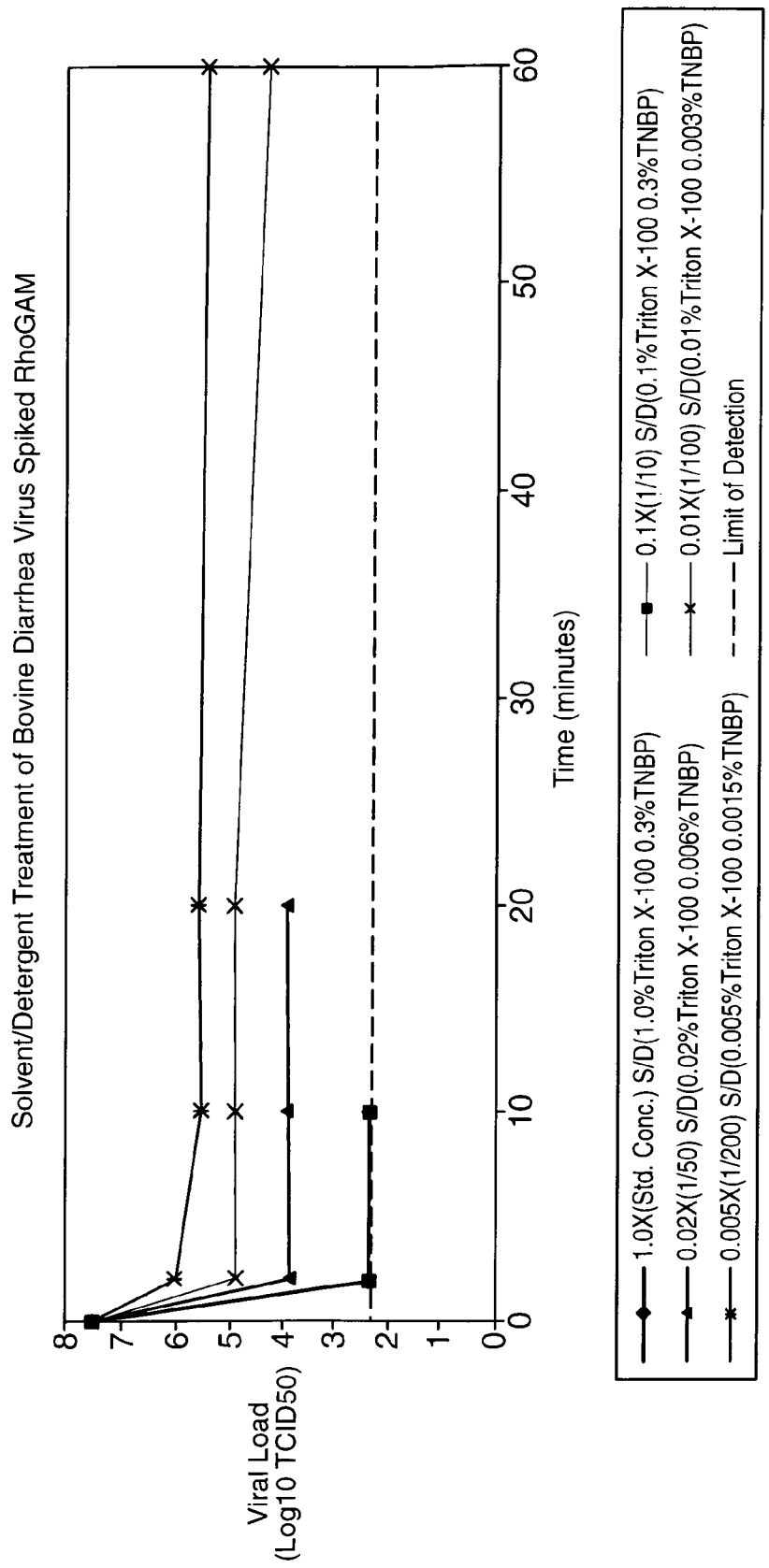
FIG. 3 is a graph showing viral inactivation using S/D treatment methods of the present invention on BVDV-spiked IgG. See Example 2 herein.

Blood plasma fractionation generally involves use of organic solvents such as ethanol, methanol or polyethylene glycol at low temperatures and at controlled pH to effect precipitation of selected plasma fractions containing desired plasma proteins. See the Cohn-Oncley fractionation (Cohn et al., supra). The resultant supernatant itself can then be precipitated until the desired degree of fractionation is obtained. With reference to FIG. 2, Fractions II and III can be further fractionated to obtain immune gamma globulin.

In the process of the invention wherein the Precipitate II (for example from the Cohn et al., supra, process) material is diluted to about 4.6-5.0 mg/ml (about 0.5%) and must be later concentrated 10× through ultrafiltration, and further wherein the preparation is treated with S/D post-manufacture, it is important to use a low initial concentration of excipient (for example, Polysorbate 80); excipient concentration in the range stated hereinabove and preferably about 0.002% does not adversely affect the process. Such adverse effect could be for example with enveloped virus, the dissociation of the virus from its envelope and the passage of virus particles into the filtrate. Studies conducted for the Assignee hereof using Vesicular Stomatitis Virus, a bullet-shaped, enveloped, RNA-containing virus showed that at the concentrations of excipient employed in this invention (100 ppm or 0.01%), no appreciable virus inactivation occurred.

The protein concentration used in the processing of the instant invention will be in the range of about 0.1% to about 1% by weight. Up to about 1% can be used where the protein material is monomeric or monoclonal. For the Precipitate II immunoglobulin used in the instant invention, the initial protein concentration used for processing is about 4.6-5.0 mg/ml (about 0.46-0.5%).

Cohn, U.S. Pat. No. 2,390,074, the contents of which are herein incorporated by reference, discloses a method of fractionating blood by which gamma globulins are prepared. The gamma globulins prepared by the Cohn method contain 19 S globulin, plasminogen and lipids. While this gamma globulin is eminently suitable for prophylaxis against diseases such as measles and tetanus, the presence of the 19 S globulin, plasminogen and lipids are unnecessary contaminants and may decrease its effectiveness in preventing immunization to the Rh-factor on the fetal erythrocytes.

The substantially pure anti-Rh globulin manufactured by the validatable processes of the present invention is prepared from human plasma which contains albumin, plasminogen, alpha, beta and gamma globulins and various lipids. Specifically, the anti-Rh globulin of the invention is a gamma globulin.

The fractionation of human plasma to obtain anti-Rh globulin is carried out according to the methods of commonly-assigned U.S. Pat. No. 3,449,314 to Pollack et al., the teachings of which patent are hereby incorporated by reference herein. With reference to the accompanying flow sheet of FIG. 2, the ability to fractionate human plasma is dependent upon the solubility of the various components of the plasma. At each stage of the fractionation, the separation of the fraction and the ultimate removal of those components which are undesirable in the anti-Rh globulin are determined by the critical control of pH, temperature, concentration of the precipitant and the ionic strength of the system.

Various organic solvents of low dielectric constant such as acetone and alcohols, precipitate proteins and have been used in the fractionation of plasma. The organic solvents utilized in the method of this invention include the various alcohols and acetone, preferably methanol. Methanol is preferable due to its comparatively lower toxicity and safer handling (e.g., explosion danger) that other organic solvents.

In order to prevent denaturation of the proteins during fractionation, precipitation is carried out at low temperatures. Since protein solubility is temperature dependent, the temperature chosen for each step of the fractionation must be the lowest possible which permits the desired separation in order to prevent denaturation.

Referring to the flowsheet of FIG. 2, the preferred method of obtaining protein in this invention, fractionation proceeds from whole human plasma. The plasma is cooled to about 1° C. and is then centrifuged to separate a cold insoluble precipitate from a supernatant. The supernatant is further fractionated to yield Precipitate I and Supernatant I. Precipitate I which consists principally of fibrinogen is discarded. Supernatant I is further fractionated to yield Supernatant II+III and Precipitate II+III. Supernatant II+III, which is discarded, contains alpha and beta globulin and lipids. Precipitate II+III consists principally of beta and gamma globulins and isoagglutinins, but also contains prothrombin, plasminogen, cholesterol and other lipids. Precipitate II+III, upon further fractionation yields Supernatant II+III W and Precipitate II+IIIW. The beta globulin, cholesterol and other lipids are largely removed in Supernatant II+III W which is discarded. Precipitate II+III W consists principally of gamma globulins, isoagglutinins, plasminogen and prothrombin and some beta globulin, cholesterol and other lipids. Upon further fractionation, Precipitate II+III W yields Supernatant III+Precipitate III. Precipitate III, which is discarded, contains isoagglutinins, plasminogen and prothrombin. Supernatant III consists principally of gamma globulins and minor amounts of fibrinogen and lipids. The final step of the fractionation yields Precipitate II which is essentially pure gamma G globulin almost completely free of 19S globulin, plasminogen and lipids. Precipitate II prepared by the process of the invention is an anti-Rh gamma globulin.

In the preferred methods of the invention, the immunoglobulin starting material for resuspension is the Precipitate II paste from the modified Cohn et al. (supra.) process. It must be noted that this initial purification of the Immune Gamma Globulin purified from plasma can also be accomplished by filtration, precipitation affinity chromatography, ion exchange or a combination of one or more of these.

The liquid diluent employed to resuspend the Precipitate II paste in the invention include the pharmaceutically acceptable diluents chosen from Water for Injection, U.S.P. ("W.F.I."), normal saline U.S.P., or any of a range of suitable buffers, the latter of which provides the advantage of providing for a stable pH. Suitable buffers are those selected from the group consisting of phosphate buffers, citrate buffers, borate buffers, acetate buffers and glycine buffers at a pH of about 6.4. Preferably the initial diluent is 3× paste by weight of W.F.I. which is later diluted in high ionic strength buffer prior to the first nanofiltration. Also suitable as the initial diluent is the high ionic strength buffer contemplated herein. Preferably an ionic strength of 150 mM±20% is employed, preferably 150 mM±20% NaCl Glycine buffer; pH 6.4.

During processing and filtration of the immunoglobulins of the invention, a high ionic strength buffer is preferably used as a processing aid to decrease the dimer and trimer formation of the immunoglobulin, allowing more complete passage through the filter. The suitable high ionic strength diluents are those recited here in above for resuspension diluents, however, at a relatively higher ionic strength and a pH of about 6.4. Preferably such processing aids are present at an ionic strength of about 150 mM±20% concentration being most preferable, which is about physiological ionic strength. In the most preferred embodiment of the invention, the high ionic strength processing aid is 150 mM NaCl-Glycine buffer, pH 6.4.

In the processing of the substantially prion- and virus-free immunoglobulins of the invention, the non-ionic excipient can conveniently be admixed with the high ionic strength buffer at the commencement of the filtration step of the process. Reference is made in this regard to Example 1A for preparation of the high ionic strength buffer containing polysorbate 80. The processing aids of the invention can be adjusted relative to each other such that ionic strength content can be reduced if polysorbate 80 concentration is increased.

In the immunoglobulin formulations of the invention and particularly the RhoGAM® and MICRhoGAM® formulations which are designed as single use parenterals, it is not necessary to employ preservatives.

In the protein concentration and organic solvent removal step of the invention for example using a second small pore size nanofiltration filter, for example, a filter from about 10,000K up to about 60,000K cutoff, for example Biomax-50 (50,000K cutoff) filter (Millipore Corporation, Bedford, Mass.) filter, the high ionic strength buffer may optionally be exchanged for relatively low ionic strength, for example 50 mM buffer. This protein concentration step serves to concentrate the nanofiltered protein product while removing some of the excipient and the organic solvent.

The filtration of the product prior to initiation of the solvent/detergent process can be any filtration or purification that will significantly reduce the potential virus load. These include but are not limited to direct size exclusion filtration, tangential size exclusion filtration, depth filtration, affinity column passage or ion exchange chromatography.

During filtration using the Viresolve-180 membrane system, the transmembrane pressure is preferably in the range of about >0 to about 3.0 psi, most preferably less than about 1.5 psi. The sieving coefficient will preferably be greater than about 60%.

The processing of the instant invention can be carried out at ambient temperatures. Processing at refrigerated temperatures will generally prolong the filtration time as such temperatures (e.g., 16-17° C.) will generally increase the viscosity. The temperature of the product during processing can be from about 0° C. or just above to about 45° C., more preferably from about 15° C.-30° C., most preferably about 20° C.-25° C.

The following terms as used herein have the meanings ascribed to them as follows:
Cross Flow Rate: Flow rate in mL/min of the feed solution across the membrane surface
Permeate: Purified product which passes through the membrane
Retentate: Material retained by the membrane
Flux: Permeate Flow Rate/Area
Conversion: Permeate Flow Rate/Cross Flow Rate
Sieving: Protein Content of Coefficient Permeate/Protein Content of Retentate In one embodiment of the instant invention, and with reference to FIGS. 1, 1A, 1B, and 1C, and U.S. Pat. No. 6,096,872, manufacture scale processing to result in substantially pure (prion- and virally-cleared) immunoglobulin, for example, RhoGAM®, by nanofiltration proceeds as follows:

Rho(D) Immune Globulin is purified to step "Precipitate II paste" using the Cohn purification method (Cohn et al., J. Am. Chem. Soc., Vol. 68, pages 459-475), in which methanol is substituted for ethanol, resuspended in Water for Injection (WFI), U.S.P. cooled to from 2-8 C. The volume of W.F.I. is calculated using the following formula:

$$\text{Precipitate II wt. (kg)} \times 3 \text{ L/kg} = \text{Req. Vol. of W.F.I. (L)}$$

Each kg of Precipitate II paste is resuspended in 3 L of W.F.I.

The admixture is vortexed (no foaming) for 3-8 hours in Hold Tank—Product (1) and stored at 4 C until further use. Steam in place (SIP) procedure is performed on the viral clearance system, which includes installation of a Viresolve CIP/SIP module (Millipore Corporation, Bedford, Mass.) into the viral clearance filter holder (2) and a Pellicon CIP/SIP module (Millipore Corporation, Bedford, Mass.) onto the ultrafiltration filter holder (3). The CIP/SIP procedure is also performed on the system and the 50 mM NaCl-Glycine Buffer storage tank (4).

The Clean in Place (CIP) procedure is a method of cleaning processing equipment without disassembly of the equipment parts. Requirements in the equipment include that all piping is stainless steel, are in proper pitch and alignment and have a minimum number of gaskets. Objectives of the CIP are to eliminate manual cleaning and cross contamination of lots. The procedure can be validated. Elements of cleaning include time, temperature, chemical and mechanical parameters. The type of residue remaining post processing will determine the cleaner that is to be used in the CIP procedure. A person having ordinary skill in the pharmaceutical processing art is familiar with the process and requirements of CIP.

Following the SIP procedure, a Viresolve-180R module, 20 stack (2) for the approximately 40 L volume of resuspended Precipitate II volume is installed in place of the Viresolve CIP/SIP module (2). (A 10 stack Viresolve-180 filter is used for 10-16 L, and a 20 stack for >16-40 L final product volume.) Four Biomax-50 cassettes (Millipore Corporation, Bedford, Mass.) are installed in place of the Pellicon CIP/SIP module (3). Two Biomax-50 cassettes are used with 10-16 L of resuspended Precipitate II volume, four cassettes are used for >16-40 L of volume. The Viresolve-180 module is sanitized with chlorine and rinsed until chlorine is determined present ≦0.3 ppm chlorine by the diethylphenylene diamine (DPD) procedure.

A pressure hold test is performed on the module (2) post-sanitation. The module must withstand a minimum of 10 psi and demonstrate a pressure drop of ≦1 psi over the required 5 minute testing period.

The Biomax-50 membranes (3) are flushed with WFI, U.S.P. Determination of Benzalkonium Chloride (Roccal) is performed on a final permeated flush sample; the benzalkonium chloride content must be ≦10 ppm. A diffusion test is performed on the Biomax-50 cassettes; release rate is calculated as follows:

$$\frac{\text{Volume}}{\text{Released (cc)}} + \frac{\text{Time}}{\text{Period (min)}} + \frac{\text{Number}}{\text{Cassettes}} = \frac{\text{Release Rate}}{\text{cc/min/cassette}}$$

The release rate must be ≦18 cc/min/cassette.

A viral clearance ultrafiltration using a Viresolve-180 filters (2) is performed on the 50 mM NaCl Glycine buffer. The viral clearance recirculation tank (T-1) (5) is charged with 50 mM NaCl-Glycine buffer. A maximum of 250 L is charged with a minimum of 130 L.

The buffer is recirculated in T-1 (5) while collecting the buffer permeate in a tank off-line.

The viral clearance recirculation tank (T-1) (5) is charged with a minimum of 60 L of the 150 mM NaCl-Glycine buffer to flush the tank and membrane.

The Precipitate II resuspension is processed as follows. Precipitate II is mixed at a rate which creates a vortex without foaming, for 15-30 minutes until completely suspended. Percent Protein by Refractive Index (mg/ml protein) is performed using hand held protometer on the Precipitate II resuspension. The required final volume of diluted Precipitate II to achieve 5.0 mg/ml protein concentration is calculated using the following formula:

$$\frac{\text{Resuspended Ppt. II Vol. (L)} \times \text{Actual Protein Conc. (mg/ml)}}{5.0 \text{ mg/ml}} = \text{Req. Dil. Ppt II Vol. (L)}$$

The required volume of 150 mM NaCl Glycine buffer is calculated using the following formula:

Req. Dil. Ppt. II Vol. (L)−Resuspended Ppt. II Vol. (L)=Vol. buffer to add (L)

Buffer is added to diluted Precipitate II and mixed at a speed sufficient to create a vortex without foaming for a minimum of 30 minutes. The admixture is stored at 15-30° C. a maximum of 2.5 hours until further processing.

The batch of diluted Precipitate II is charged into the viral clearance recirculation tank (T-1) (5) for ultrafiltration. The TMP setpoint is set at about 3.0. However, it may go higher however if it reaches about 12 the membrane may be polarized and the retentate should be permitted to wash the membrane (by reducing the permeate). The Viresolve level setpoint is calculated as follows:

$$\frac{\text{Total Vol. of Diluted PPT II (L)}}{3} = 1/3 \text{ Total Vol. (L)}$$

If the above result is <50, 50 was entered as the Viresolve level setpoint setting. The ⅓ total volume is rounded to the nearest whole L.

The blood components, blood plasma or any fraction, concentrate or derivative thereof containing blood proteins, plasma-containing products and plasma fraction-containing products containing labile proteins, for example immunoglobulins:

$$\frac{\text{Total Vol. of Diluted PPT II (L)}}{12} = \text{Conc. endpoint}$$

If the above result is <20, 20 was entered as the conc. endpoint. The ultrafiltration diafiltration endpoint is calculated as follows:

Conc. endpoint−3=Diaf Endpoint

The diafilter total setpoint is calculated as follows:

Conc Endpoint×5.5=Diafilter total Setpoint (L)

To begin the ultrafiltration/concentration process, the Viresolve-180 feed pump (P1) (7) rate is ramped to 75%-83% for the 20 stack, or 37%-42% for the 10 stack filter size. The TMP control is engaged; the TMP is controlled by the rate of the permeate pump (P2); if the transmembrane pressure goes to 3.0 then the pump will slow down. The Viresolve permeate pump (P2) (8) rate is ramped slowly up to 18%, or 9% for the 10 stack filters. Once P2 is ramped up, a retentate pressure (PT3) of ≧5.0 psi is maintained. Once the TMP equilibrates, the pump rate range is set to 9%-11% for the 10 stack filter; 18%-23% for the 20 stack filter. The TMP pressure is not controlled; however, it is preferably relatively low, e.g., at about less than 3.0 psi, or the membrane may become polarized. Should the TMP become higher, for example 3.0 psi, the permeate may be stopped so the retentate can wash the membrane. The UV meter (UV1) (9) should be between the lower limit of 4.0 A.U. and the upper limit of 7.7 A.U. The permeate flow (FT1) is between the lower limit of 0.81 liter/min (LPM) and the upper limit of 0.98 LPM; between 0.40 LPM-0.49 LPM for a 10 stack filter. The processing temperature is maintained at about 15-30° C. These conditions are monitored throughout the viral clearance/ultrafiltration process. The UV meter (UV1) (9) is between the lower limit of 6.4 A.U. and the upper limit of 7.7 A.U. Sieving coefficient should be about ≧75%.

When the T-2 (6) volume reaches approximately 75-100 L, the Pellicon System (3) is set up and begun mixing. The UF feed pump (P5) (10) is started/ramped up, and the UF permeate flowrate controlled by the pump rate. The UF feed pressure (PT4) and UF retentate pressure (PT5) is maintained as follows:

UF Feed Pressure: ≦30 psi
UF Retentate Pressure: ≦10 psi

A differential is maintained between feed pressure and retentate pressure of ≦20 psi Feed pressure (psi)−retentate pressure (psi)=differential (psi)

The volume levels in the diluted Precipitate II feed tank T-1 (5) is monitored (by weight) and responded to by load cells on T-1.

Constant volume diafiltration is performed in T-1 (5). This diafiltration is used to wash the residual protein through the system and the Viresolve-180 membrane thereby increasing the yield. A 3×150 mM NaCl-Glycine buffer diafiltration is performed; a set amount of buffer is added at the same rate that it is being removed through the Viresolve-180 permeate. Once the diafiltration steps are completed, T-1 (5) and the Viresolve-180 module (2) are sanitized as described hereinabove, using the chlorine process, insuring that any virus held up will be inactivated. The bulk in T-2 (6) is concentrated by constant volume diafiltration in T-2 (6), with the virally-cleared 50 mM NaCl-Glycine buffer. This step concentrates the bulk product and exchanges the higher ionic strength buffer concentration for a lower ionic strength concentration, removes the methanol from the Cohn process, and about half the polysorbate 80. After the diafiltration process is completed, the level in T-2 (6) is recorded in liters. A sample is drawn from T-2 (6) to perform a digital specific conductance determination on the UF permeate sample. The result must fall between 4.95-5.67×10−3 mhos/cm. If the requirement is not met on the first test, constant volume diafiltration must be continued until the test result is within this required range.

T-2 level after the 5.5× diafiltration should be ≦95% of the resuspended Precipitate II volume. If T-2 level is >95% of the resuspended Precipitate II volume, continue to concentrate the bulk until the T-2 volume meets the upper volume level requirement. Once the volume level is met, the UF permeate is shut off (11) and the bulk mixed by recirculation, and a 10.5 ml sample aseptically removed (12). Percent protein determination is made by refractive index using the hand held protometer on a 0.5 ml aliquot of the sample. If the protein concentration is not at least about 5.5%, the sample must be further concentrated until such minimum percent is met. The bulk is moved to an interim vessel and the bulk weight is calculated gravimetrically using the following formula:

$$\text{Filled Interim Vessel Weight(kg)} - \text{Interim Vessel Tare Weight(kg)} = \text{Bulk Product Weight in } T\text{-}2 \text{ (kg)}$$

Bulk adjustments can be made by determining the volume of 50 mM NaCl-Glycine buffer to add to achieve final bulk volume by using the following formula:

$$\frac{\text{Actually\% Protein} \times \text{Bulk Volume(L)}}{\text{Desired\% Protein(5.0\%)}} = \text{Required Final Volume(L)}$$

The required volume of 50 mM NaCl-Glycine buffer to add is calculated as follows:

$$\text{Required Final Volume(L)} - \text{Bulk Product Volume in } T\text{-}2 \text{ (L)} = \text{Required Volume of 50 mM NaCl-Glycine}$$

An initial pH determination is made on the remaining sample aliquot, by first diluting the aliquot 1:10 with 0.9% NaCl and titrated to a pH of 6.3-6.4 with 1:100 dilution of 0.5N HCl or 0.5N NaOH.

If adjustment is required, the amount of undiluted 0.5N reagent required to adjust the pH of the bulk is calculated as follows:

$$\text{Required Final Volume(L)} - \text{Volume of 1:100 titrant required(ml)} = \text{Volume of undiluted 0.5 N reagent(ml)}$$

Integrity testing is performed on the Viresolve-180 filter module in accordance with accepted methods. The integrity test value must be ≧1.2, and the module must be sanitized with chlorine as above and rinsed.

50 mM NaCl-Glycine buffer is added to the bulk as calculated by the following formula:

$$\text{Tank 2 Level(L)} + \text{Required Volume of 50 mM NaCl-Glycine Buffer(L)} = \text{Tank 2 Level for Required Final Volume of Bulk}$$

The bulk is pumped back into T-2 and continued to mix in T-2 for 10-60 minutes after required final volume was reached, then 10.5 ml aliquot of bulk product is aseptically removed for determination of pH. pH must be 6.3-6.4. If pH is outside of the stated range, an aliquot must be diluted and titrated to the acceptable pH as before and the required amount of undiluted 0.5N reagent must be calculated and added back into the bulk while mixing, as hereinabove.

The percent protein is determined by refractive index using the hand-held protometer as above. If the protein concentration is ≧5.0%, which is acceptable, the bulk may pass through to the next step.

The bulk is optionally filtered through a 0.2μ Optiseal filter (13), with the pressure not exceeding 15 psi during the filtration process, then the bulk is microbiologically and serologically tested.

A clean-in-place procedure, consisting of rinsing with WFI and steam, is performed on the viral clearance system (CIP procedure described hereinabove).

Acceptance criteria for the product are listed in Table 1.

TABLE 1

| Characteristic | Requirement |
| --- | --- |
| Protein | 4.0 to 6.0% |
| pH | 6.3 to 6.4 |
| Polysorbate 80 | 80 to 200 ppm |
| Methanol Content | <50 ppm |

The present invention is directed to contacting with a solvent any of the protein containing compositions listed hereinabove for example a blood product. In particular, such blood product is preferably a human immune gamma globulin fractionated in accordance with the modified Cohn-Oncley cold alcohol fractionation scheme as disclosed in Cohn et al., supra and in co-assigned U.S. Pat. No. 6,096,872. After the isolation of the IgG the solution is processed through a Millipore Viresolve size exclusion filter to remove enveloped and non-enveloped viruses. The virally-cleared material is then diafiltered and concentrated using a Millipore BioMax (50,000 MW) size exclusion filter. It is at this stage in the manufacturing process for RhoGAM® that the S/D process is preferably used.

The protein composition in particular human immune gamma globulin seeking to be treated for viral inactivation in accordance with the instant invention, including the human immune gamma globulin or RhoGAM®, is contacted with a solvent for example a dialkylphosphate or trialkylphosphate having alkyl groups which contain 1 to 10 carbon atoms, especially 2 to 10 carbon atoms, for example trialkylphosphates including tri-(n-butyl) phosphate, tri-(t-butyl) phosphate, tri-(n-hexyl)phosphate, tri-(2-ethylhexyl) phosphate, tri-(n-decyl)phosphate. An especially preferred trialkylphosphate is tri-(n-butyl)phosphate. Mixtures of different trialkylphosphates can also be employed as well as phosphates having alkyl groups of different alkyl chains for example, ethyl, di(n-butyl)phosphate. Similarly the respective dialkylphosphates can be employed including those of different alkyl group mixtures of dialkylphosphates. Furthermore, mixtures of di- and trialkylphosphates can be employed.

When the S/D process is employed after the final size exclusion filtration (post manufacture) as is the preferred embodiment, the trialkyl phosphate solvent used is most preferably tri(n-butyl)phosphate (TNBP) at a concentration ranging from about 0.003% to less than 0.3%, more preferably from about 0.006% to less than 0.3%, more preferably from about 0.015% to about 0.15% %, more preferably from about 0.03% to about 0.15%, and most preferably from about 0.03% to about 0.06%, which for comparative purposes to the concentrations used in the prior art is about 1.0-0.3% mg/ml. In a preferred embodiment the solvent concentration used is about 0.06%.

The di- or trialkylphosphate solvents can be used either with or without the addition of a surfactant, i.e., a detergent. It is preferable however to use di- or trialkylphosphate in conjunction with a detergent. Such detergent can be added either before, simultaneous with or after the di- or trialkylphosphate contacts the blood product composition. The purpose of the detergent is to enhance the contact of the virus in the blood product composition with the di- or trialkylphosphate. It is a preferred embodiment to expose the protein composition to be viral inactivated with a pre-mixed solution containing the S/D in combination.

Preferred detergents are the non-ionic detergents. In particular there are contemplated those detergents which include the polyoxyethylene derivatives of fatty acids, partial esters of sorbital anhydrides, for example, those products known commercially as Tween 80® and Tween 20®, for example and polysorbate 80, also those nonionic oil soluble water detergents such as that sold commercially under the trademark Triton X-100® (oxyethylated alkylphenol). Also contemplated is sodium deoxycholate as well as the "Zwittergents" which are synthetic zwitterionic detergents known as "sulfobetaines" such as N-dodecyl-N,N-methyl-2-ammonio-1 ethane sulphonate and its congeners, or non-ionic detergents such as octyl-beta-D-glucopyranoside. The detergent Triton X-100 is used in the preferred embodiments of the instant invention due to its superior synergistic viral inactivation when used in combination with solvent.

Substances which might enhance the effectiveness of alkylphosphates include reducing agents such as mercaptoethanol, dithiothreitol, dithioerythritol, and dithiooctanoic acid. Suitable nonionic surfactants are oxyethylated alkyl phenols, polyoxyethylene sorbitan fatty acid esters, polyoxyethylene oils and polyoxyethylene alcohols and polyoxyethylene oxypropylene fatty acids. Some specific examples include the following: alkylphenoxypolyethoxy (30) ethanol, polyoxyethylene (20) sorbitan monolaurate, polyoxyethylene (20) sorbitan monopalmitate, polyoxyethylene (20) sorbitan monostearate, polyoxyethylene (20) sorbitan monooleate, polyoxyethylene (20) sorbitan tristearate, polyoxyethylene (20) sorbitan trioleate, polyoxyethylene (20) palmitate, polyoxyethylene (20) lauryl ether, polyoxyethylene (20) cetyl ether, polyoxyethylene (20) steryl ether, polyoxyethylene (20) oleyl ether, polyoxyethylene (25) hydrogenated castor oil, and polyoxyethylene (25) oxypropylene monostearate.

The amount of detergent, if employed, ranges from about 0.01% to less than 1.0%, more preferably from about 0.02% to less than 1.0%, more preferably from about 0.05% to about 0.5%, more preferably from about 0.1% to about 0.5%, and most preferably from about 0.1% to about 0.2%. When the S/D process is employed after the final size exclusion filtration (post-manufacture) as it is the preferred embodiment using human immune gamma globulin, the detergent used is most preferably Triton X-100 at about 0.1% to 0.2%, with 0.2% most preferred which for comparative purposes to the concentrations used in the prior art is about 1.0%.

The S/D combination and ratio preferably employed in the methods of the instant invention, that is, tri(n-butyl)phosphate (TNBP) at about 0.03% to about 0.06% and Triton X-100 at about 0.1% to about 0.2%, is most preferred under the incubation conditions employed due to its robust viral inactivation; the data herein shows the viral inactivation is completed as quickly as the reaction is quenched.

The treatment of blood product compositions with the solvent/detergent as contemplated by this invention is effected at a temperature between about −5° C. and 70° C., preferably between about 15° C. and 25° C. The time (contact) for such treatment is for at least about 1 minute, preferably about 10 minutes to about 1 hour and most preferably about 1 hour. The treatment is normally accomplished at atmospheric pressure, although both sub- and super-atmospheric pressures can be used. When in accordance with a preferred embodiment of the invention, it is employed TNBP at about 0.06% and Triton X-100 at about 0.2%, treatment is performed for about 1 hour at 15° C. to about 25° C. Increases in temperature, incubation (contact time) and pressure would be expected to affect the amount of solvent and detergent used (requiring less therefore), to result in the same effect.

Protein recovery depends on detergent-protein mixing method. The method of mixing the detergent (e.g., the Triton X-100) with the final human immune gamma globulin affects the protein recovery post S/D treatment. Adding undiluted detergent directly to the protein, in this case the human immune gamma globulin, results in protein recovery of only 80-90%. It is theorized that such a method caused protein-detergent binding, and removal of the detergent resulted in a co-removal of the protein. A more preferable method uses a 10% solution of detergent (with 3% TNBP) added to the protein solution in order to achieve the aforementioned S/D concentrations, and protein yields are thus 95% or greater.

It is critical to the viral inactivation process to know the amount of S/D that is being added to the resuspended precipitate II material (from the Cohn-Oncley cold alcohol fractionation procedure; see Cohn et al., supra) (or to the plasma derivatives purified by other methods or combinations of alcohol fractionation, precipitation or affinity chromatography, etc.). It is similarly important to be able to determine that the residual amount of the S/D post removal is less than about 10 ppm. The amount of S/D delivered to the product can be determined by weight and volumetric measurement. Measurements of polysorbate 80 and Triton X-100 can be measured spectrophotometrically and via HPLC; TNBP can be measured by gas chromatography. For example, reference is drawn to Milwidsky, A., Analyst 1969; 94:377-86 (for polysorbate 80); Karlsson, G et al, J. Chromatography A 2002; February 8; 946 (1-2): 163-168 (for Triton X-100); and Nellaiappan K et al., J. Chromatography B Biomed Sci Appl.; 2001; June 5; 757(1):181-189 (for TNBP).

Normally, after treatment of the protein-containing composition, the S/D are removed although such may not be necessary if using the methods of the instant invention. This is due to the relatively low concentration of S/D and will also depend on the nature of the virus-inactivating agents and the intended further use and processing of the protein containing composition for example a blood product composition, so treated.

Removal of the S/D materials is preferred in the embodiment of viral inactivation of human immune gamma globulin. Typical methods for S/D removal include passage through a C-18 column, diafiltration through membranes, which retain either the S/D or the blood product composition of interest, adsorption of the S/D or the blood product composition of interest onto chromatographic or affinity chromatographic supports. Several additional methods include ultrafiltration, filtration/adsorption, i.e. by filters containing diatomaceous earth i.e. the Cuno Delipid Plus and the filter's amorphous precipitated silica Sipernat 50S used along as an adsorbent and removed from the composition by centrifugation, for example.

A preferred S/D removal method is the use of adsorbents. Two chromatographic adsorbents are preferred. The first and most preferable adsorbent, SDR HyperD Solvent-Detergent Removal Sorbent (Ciphergen Corporation, Fremont, Calif.) is a silica bead with an added three dimensional cross-linked hydrophobic polymer specifically made to remove Triton X-100 and TNBP from S/D processes. The second, Amberchrom CG161C (Rohm and Haas, Philadelphia, Pa.) is a divinylbenzene polymer resin used as both an adsorbent and in reverse phase liquid chromatography. The results with both materials have been excellent. Both adsorbents are effective at removing Triton X-100 and TNBP to levels below 1 ppm from S/D treated RhoGAM® containing 10,000 ppm Triton X-100 and 3000 ppm TNBP. Both flow rate through the column and temperature effect the removal of the S/D reagents. Lower flow rates and ambient temperature (vs. colder temperatures) increase the amount of S/D reagents removed from RhoGAM® before breakthrough occurs.

The SDR Hyper D column is the preferred embodiment as gravity feed of the S/D RhoGAM® is possible, although a peristaltic pump is used to control the flow rate. This ability to gravity feed has led to the development of a simple way to remove S/D reagents from a large number of samples using disposable columns. This method has allowed the removal of S/D reagents from biological fluids in viral inactivation studies, eliminating the need to dilute the samples 100- to 1000-fold to eliminate the toxic effects of the S/D reagents. This has led to a 2-3 log increase in assay sensitivity.

It was also determined that the diffusion chromatography column was able to remove polysorbate 80 along with the solvent/detergent reagents used to inactivate the product.

In a preferred embodiment of the invention, when the viral inactivation is performed on human immune gamma globulin also known as RhoGAM® or MICRhoGAM®, removal of the S/D post treatment is preferably accomplished by the use of the S/D removal sorbent. As discussed hereinabove, the preferred sorbent is made of silica beads in which the pore volume is filled with a three dimensional cross-linked hydrophobic polymer. S/D residual observed after exposure to a column of said material is in the low parts per million (ppms). A SDR Hyper D column (Ciphergen) may be used as a one-time sorbent or may be reconditioned/regenerated by removal of the S/D. After removal of the S/D using the sorbent, the globulin solution is passed over a Biomax 50 filter (Millipore Corporation) to exchange the buffer to the final formulation, see FIG. 1.

The methods of the invention can be combined with other modes of viral inactivation methods including those for non-lipid coated viruses, such as for example, heating of the blood product composition.

Herein disclosed are data of samples of the blood product material obtained after nanofiltration methods (post-manufacture) which were spiked with virus and subjected to solvent-detergent treatment at a 1/2000 manufacturing scale with concentrations ranging from less than 1.0% Triton X-100 and less than 0.3%, tri-n-butyl-phosphate (TNBP) to about 0.005% Triton X-100 and about 0.0015% TNBP. Aliquots of each treated sample were removed at various intervals during the treatment and either diluted to stop the inactivation or passed through a solvent-detergent sorbent column (SDR HyperD Solvent-Detergent Removal Sorbent (Ciphergen Biosystems). Virus titers were determined by standard methodology, of $TCID_{50}$ (regarded in the art as the quantity of virus in a specified suspension volume that will infect 50% of a number of cell culture microplate wells, or tubes, termed the TCID50 or Tissue Culture Infectious Dose 50).

In particular contrast to prior methods of S/D inactivation step performed pre-manufacture or the front end, for example on the source plasma (Piet M P J, et al., Transfusion 1990; 30:591-598), or on an intermediate in the process, for example whereas a size exclusion step to remove viruses is placed at the end of a process (Van Holten R W, et al., Vox Sang 2002; 83:227-233; and Burnouf T, et al., Haemophilia 2003; 9;24-37), the placement of the S/D viral inactivation step in this sequence may be because of historical reasons and may not be optimal. In the instant invention placement of the S/D step is towards the end of the manufacturing process (post-manufacture), after virus removal by tangential flow nanofiltration.

Solutions and compositions as listed hereinabove can be purified using the methods of the instant invention to an extent of virus inactivation of greater than 4 logs of virus such as Hepatitis B and C and having a suitable protein yield, for example at least about 80%, preferably at least 85%, more preferably about 95%, and most preferably 98% to 100%.

Preferably contemplated in the invention is a fractionated human immune gamma globulin which is substantially free of lipid-coated virus such as Hepatitis B and C to an extent of having an inactivation of greater than 4 logs of the virus and a yield of protein activity of least about 80%, preferably at least 85%, more preferably about 95%, and most preferably 98% to 100%.

Protein activity of the components treated by the methods of the invention can be measured by standards techniques well known in the art for measuring protein activity.

The solvent-detergent treatment of the invention was found to be effective at concentrations of solvent and detergent significantly lower than previously reported. In particular, the concentrations of solvent and detergent necessary for robust inactivation of viruses may be significantly less than traditionally used. Product purity and absence of interfering substances (i.e. lipids) may affect the kinetics of viral inactivation. Reduced levels of solvent and detergent lead to greater efficiencies in their removal post-inactivation with the potential for greater yields and decreased processing costs.

Placement of the S/D step towards the end of the manufacturing process (and in particular in a preferred embodiment, after virus removal by tangential flow nanofiltration) has the following advantages:

1. The product is well defined and uniform at the final stages of the purification process, allowing for reduced amounts of S/D to be used;
2. Removal of the S/D can be accomplished more efficiently because of the reduced volume; and
3. Removal of viral load by nanofiltration prior to S/D treatment leaves the possibility of less viral debris in the final product, decreasing the possibility of a positive viral PCR assay.

The introduction of lipid into the S/D mix when treating the blood product results in the quenching of the viral inactivation for test viruses bovine viral diarrhea virus (BVDV) and West Nile virus (WNV). This observation may partially explain why the S/D treatment of plasma (front end processing) requires longer time and increased S/D concentrations to obtain the same effect as observed with less reagents; treatment of plasma is normally performed at a higher concentration of solvent than that used for plasma purified products such as Factor VIII (Horowitz, B et al., Blood, Vol 79(3) 1992 pp 826-831).

The ability to treat the product post manufacture (post-purification, for example, via size exclusion filtration) results in less protein being introduced to the column. This is significant if a manufacturer was unable to validate the regeneration of the column used to remove the detergent.

It is also reasonable to conclude that there is less chance of viral debris detection by nucleic acid testing if the product passes through a size exclusion filter prior to S/D treatment. S/D or pasteurization destroys the infectivity of the viruses tested however will not affect the PCR titers (Hilfenhause, J et al., Transfusion, Vol. 37, September 1997, pp 935-940).

It is surprising that the solvent portion of the solvent/detergent treatment can be reduced by 100 fold without sacrificing the viral inactivation kinetics of enveloped virus. In the embodiment of the invention wherein S/D treatment is performed at the front end (in a heterogeneous system such as pooled plasma), it is prudent to have higher amounts of TNBP and Triton X-100, as well as the incubation time to always be in sufficient excess to allow for variables such as viral load or the lipid content of the plasma. We have found that with the pretreatment of plasma with Aerosil 380 (Degussa AG, Dusseldorf, Germany) prior to solvent/detergent we can enhance the viral inactivation.

The placement of the solvent-detergent step earlier in the fractionation/purification process is advantageous in cases where one or more of the manufacturing steps already in place achieve the removal of the solvent-detergent chemicals. In cases where the target protein is adsorbed onto a chromatographic resin, the TNBP and detergent will pass through the column along with other contaminates and are subsequently washed out prior to elution of the target protein However, with the use of specific adsorbents that can efficiently remove both TNBP and detergent simultaneously such as the preferred SDR Hyper D adsorbent as used herein, the S/D step can be performed anywhere in the manufacturing process.

Placement of the S/D treatment at the end of the process has the advantage of requiring less TNBP and detergent, since the volume of purified protein to be treated should be significantly reduced. This would also proportionally decrease the amount of sorbent necessary to remove the S/D chemicals. Exposure to TNBP would be reduced. In this instance, a 40 liter full-scale lot of anti-D immune globulin would require less than $1/20^{th}$ the amount of S/D chemicals that would be used to treat the 900 liter starting plasma pool.

Beyond the reduction in S/D obtained by placing the viral inactivation step at the end of the manufacturing process, the current invention evaluates kinetics of viral inactivation with reduced volumes of both TNBP and Triton X-100.

The data herein shows that initial runs with BVDV and PRV indicated that dilutions of Triton X-100 and TNBP as low as $1/50^{th}$ the standard concentrations of 1.0% Triton X-100 and 0.3% TNBP were sufficient to inactivate the viruses to the limit of detection. The data also showed that the inactivation occurred rapidly; virtually all inactivation that occurred for any given sample happened within the first two minutes with no additional inactivation beyond this interval (FIGS. 3-6).

Figure 4:
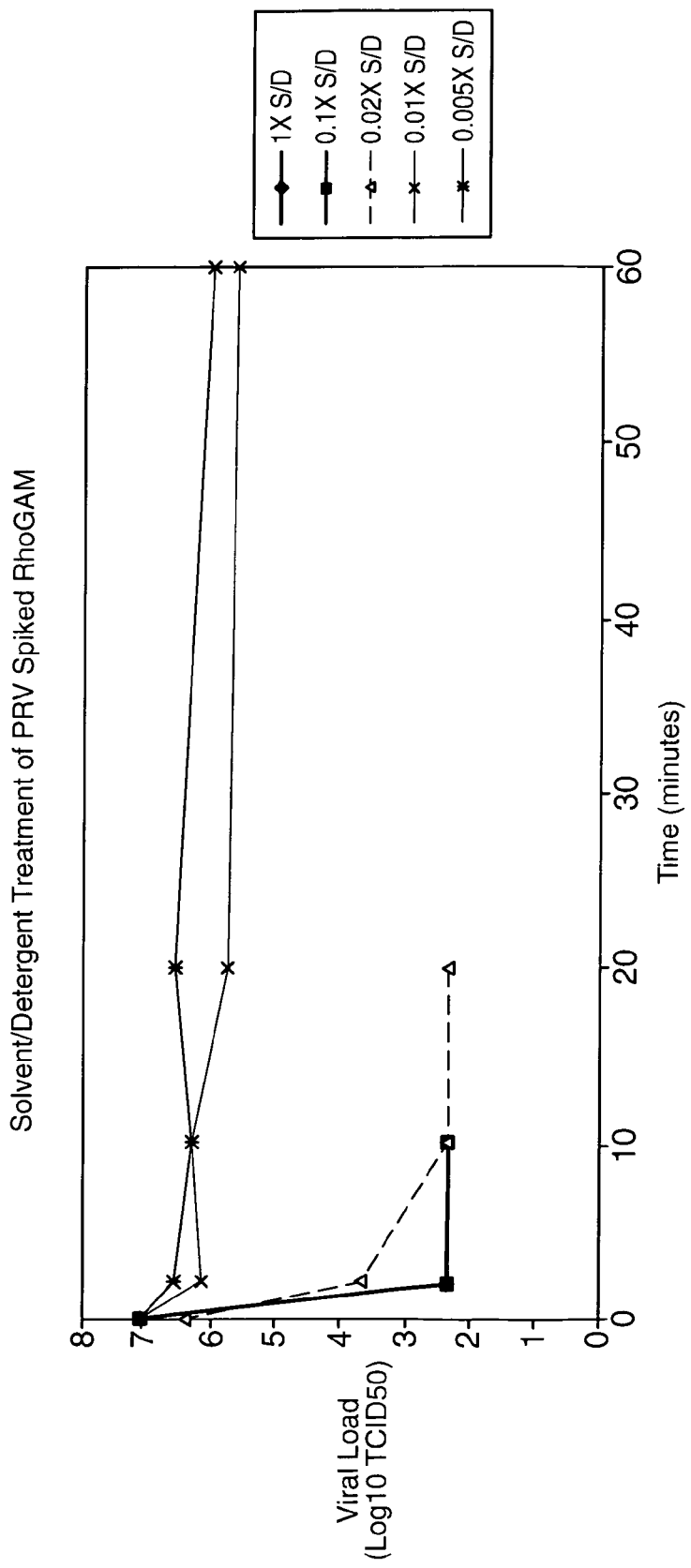
FIG. 4 is a graph showing viral inactivation using the S/D treatment methods of the present invention on PRV-spiked IgG. See Example 2 herein.

The silica diffusion sorbent SDR Hyper D solvent-detergent removal sorbent (Ciphergen) is an efficient means of removing both Triton X-100 and TNBP simultaneously from S/D treated material. The effect of the SDR Hyper D on virus titers without the presence of S/D was determined by passing virus-spiked samples through a column of SDR HyperD in a proportion less than that used to remove the standard concentrations of Triton X-100 and TNBP. Using a less than normal volume would accentuate any removal of virus from the samples. There was no significant reduction in BVDV (FIGS. 3 and 5) and an approximately 1-log reduction in PRV (FIG. 4). This loss of PRV may possibly be attributable to the large size of PRV (120-200 nm), causing retention by the sorbent; the relatively smaller BVDV (50-70 nm) is not retained. We have also observed that the time of incubation at 15° C. is the determining factor in PRV removal.

Figure 5:
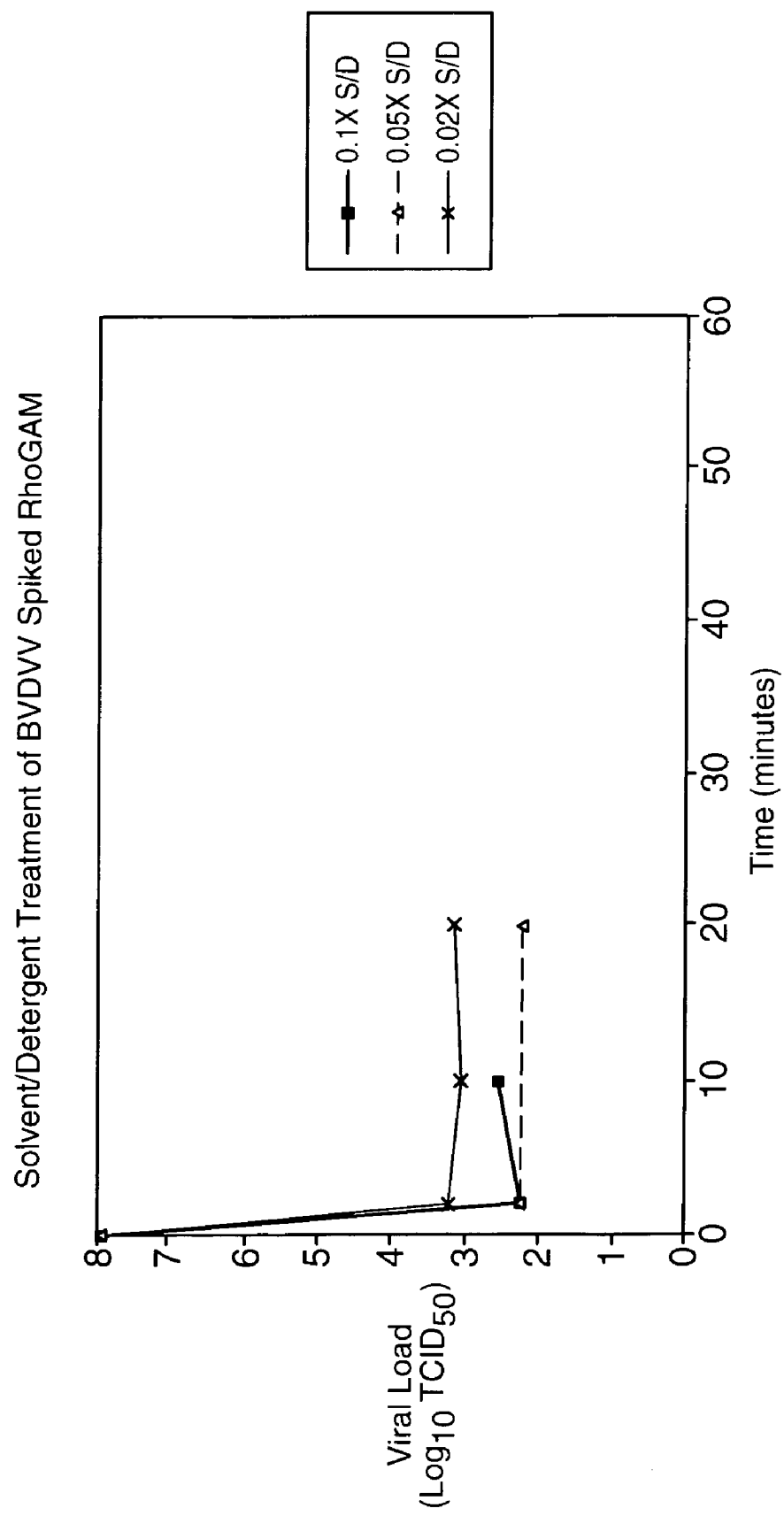
FIG. 5 is a graph showing viral inactivation using the S/D treatment methods of the present invention on BVDV-spiked IgG. See Example 2 herein.
Figure 7:
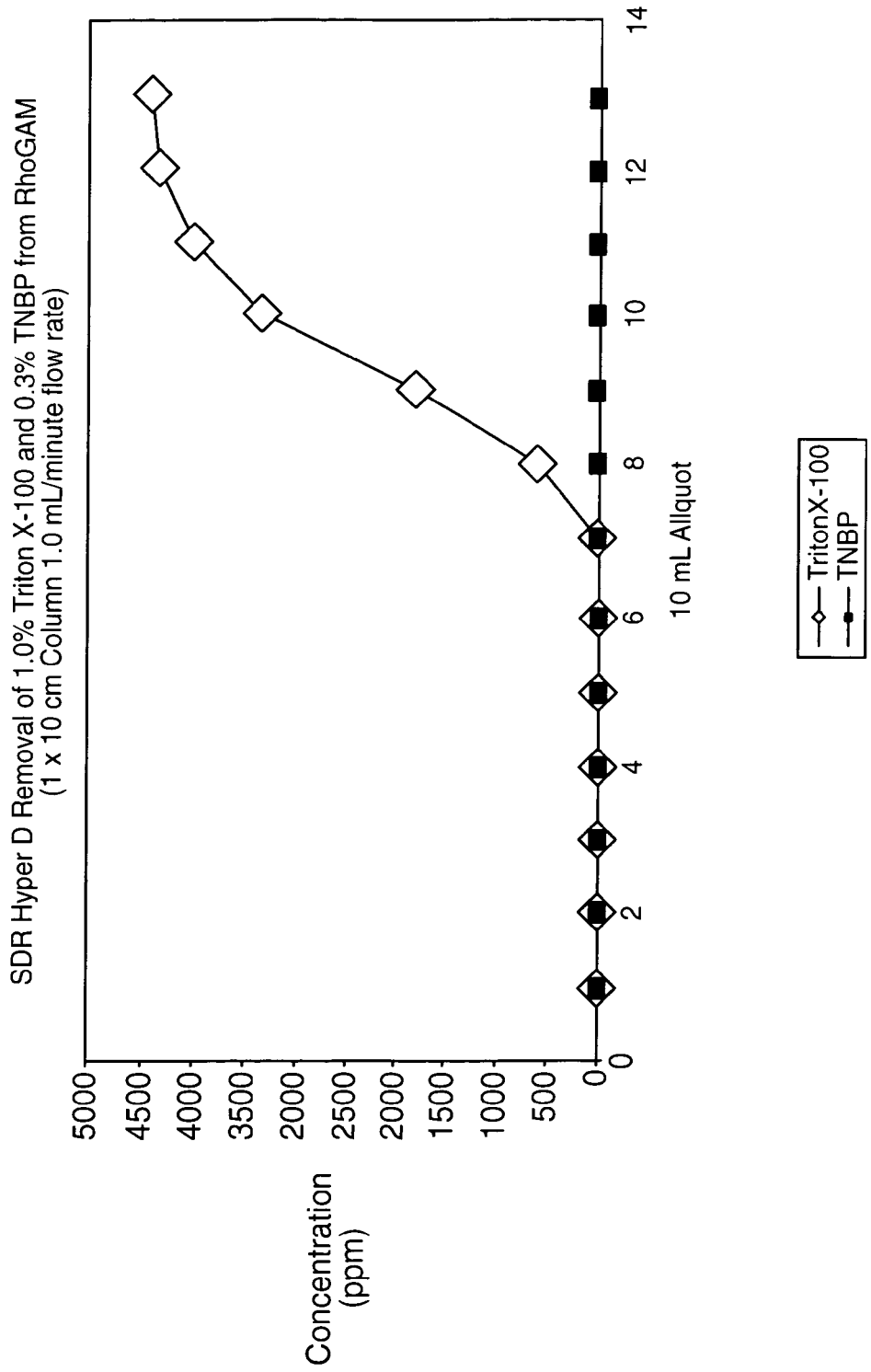
FIG. 7 is a graph showing assessment of the capacity of the SDR Hyper D sorbent to remove Triton X-100 and TNBP. Triton X-100 breakthrough was observed after 70 mL passed through the column. No breakthrough was seen for the TNBP indicating that the Triton X-100 concentration will be the critical parameter in calculating the amount of sorbent required.

Since the first runs showed inactivation to the lowest S/D dilution ($1/50^{th}$) tested, in the second set of runs with BVDV and PRV, additional dilutions of S/D ($1/100^{th}$ and $1/200^{th}$) were evaluated. Post S/D treated samples were passed through disposable SDR Hyper D columns to remove the S/D chemicals. The column treatment allowed the samples to be tested undiluted, rather than diluting them 1/100 in buffer, thus enhancing the sensitivity of the viral assays. The sensitivity of the BVDV assay was increased by 2-3 logs (FIG. 6) and the PRV assay by one log. The 1 log increase seen with PRV rather than the expected 2-3 logs is consistent with the 1 log reduction attributed to the SDR HyperD. Both the $1/100^{th}$ and $1/200^{th}$ S/D treatments gave incomplete inactivation. Additionally, the $1/50^{th}$ dilution of S/D that had showed BVDV inactivation to the limit of detection in the first run now showed incomplete inactivation with the increased assay sensitivity (FIG. 5). PRV continued to show complete inactivation to the limit of detection at the $1/50^{th}$ dilution.

With the virus contamination being controlled by prefiltration one may be able to optimize this sorbent process. Process cost and time can be reduced by adding less reagent, reducing the incubation time and reducing the amount of resin required to remove the reagents.

Robustness of the treatment at the reduced concentration of reagent and the less harsh incubation conditions were challenged by performing a second viral spike post the initial incubation in the S/D milieu. This dual challenge reinforces that even at the reduced S/D and incubation times the treatment is robust. See Table 2 and Example 2.

TABLE 2

Solvent/Detergent Treatment of BVDV Spiked RhoGAM
0.2 × S/D (0.2% Triton X-100 0.06% TNBP)

| Sample | Viral Load ($Log_{10}$ $TCID_{50}$) |
| --- | --- |
| Spiked Load | 7.83 |
| Hold Control I | 6.19 |
| Hold Control II | 5.87 |
| S/D T = 0 minutes | 2.64 |
| S/D T = 10 minutes | 2.64 |
| S/D T = 60 minutes | 2.64 |
| Respike into S/D treated RhoGAM | 7.83 |
| T = 10 minutes post respike | 1.69 |

In our hands, concentrations of S/D that were 50 times less concentrated that the normal 0.3% TNBP 1.0% Triton X-100 resulted in significant inactivation over a relatively short time period.

As a result of the increased appearance of West Nile Virus in the continental United States in recent years (Biggerstaff et al., Transfusion 42, August 2002 pg 1019-1026), we compared the effect of S/D on both viruses WNV and BDVD. We confirm results of other investigators (Remington K M et. al., Vox Sang. 2004 July; 87(1) 10-18) that BVDV and West Nile virus are very similar in their physiochemical properties. This similarity can be observed by comparing the inactivation kinetic profile of both viruses. Compare FIGS. 3-6. Similarity in the time and S/D concentration required to inactivate, was observed.

Throughout this application, various patents and papers are referenced. The disclosures thereof in their entireties are hereby incorporated by reference into this application in order to more fully describe the state of the art as known to those skilled therein as of the date of the invention described and claimed herein.

The following examples are provided for the purposes of illustration only and are not to be viewed as a limitation of the scope of the invention.

EXAMPLES

Example 1

Manufacture of virally-cleared RhoGAM® by ultrafiltration proceeded as in U.S. Pat. No. 6,096,872 with the following modifications:

Rho(D) Immune Globulin 6.802 Kg purified to step "Precipitate II paste" using the modified Cohn purification method was resuspended in 20.406 L of Water for Injection (WFI), U.S.P. cooled to 4° C. The admixture was vortexed (no foaming) for 4 hours, and stored at 4° C. until further use.

Following the SIP procedure, a Viresolve-180R module (Millipore Corporation) (20 stack) for the approximately 27.208 L volume of resuspended Precipitate II volume was installed. Two Biomax-50 cassettes were installed in place of the Pellicon CIP/SIP module. The Viresolve-180 module was sanitized with chlorine and rinsed as described hereinabove. The Biomax-50 membranes were flushed with WFI, U.S.P. Determination of Benzalkonium Chloride (Roccal) was performed on a final permeated flush sample; the benzalkonium chloride content was 8 ppm. A diffusion test was performed on the Biomax-50 cassettes; release rate was calculated as described hereinabove; total volume released was 22 cc in 5 minutes, and the actual release rate was 4.4 cc/minute.

A viral clearance ultrafiltration using a Viresolve-180 was performed on 245 L of the 50 mM NaCl Glycine buffer. The viral clearance recirculation tank (T-1) was charged with 245 L of 50 mM NaCl-Glycine buffer. The buffer was recirculated in T-1 while collecting the buffer permeate in the previously-sanitized 50 mM NaCl-Glycine buffer storage tank off line. Volume of permeated buffer collected was 213 L. Virally cleared buffer was stored at ambient temperature of about 63-78° F.

A 150 mM NaCl-Glycine buffer (see Example 1A for preparation) flush was performed by attaching the buffer feed tank to the viral clearance recirculation tank (T-1). T-1 was charged with 60 L of the 150 mM NaCl-Glycine buffer to flush.

The Precipitate II resuspension was processed as follows. The Precipitate II (6.802 Kg) was mixed at a speed creating a vortex without foaming, for 55 minutes, until completely suspended. Percent Protein by Refractive Index (mg/ml protein) was performed using hand held protometer on the Precipitate II resuspension, and was 59 mg/ml.

The required volume of diluted precipitate II was calculated to achieve a protein concentration of 5.0 mg/ml:

$$\frac{\text{Actual Ppt. II Vol. (L)} \times \text{Actual Protein Conc. (mg/ml)}}{5.0 \text{ mg/ml}} = \text{Req. Dil. Ppt. Vol. (L)}$$

OR $$\frac{(27.208 \text{ L}) \times (59.0 \text{ mg/ml})}{5.0} = 321.054 \text{ L Dil. Ppt. II vol.}$$

The required volume of 150 mM NaCl Glycine buffer was calculated using the following formula:

Req. Dil. Ppt. II Vol. (L)−Resuspended Ppt. II Vol. (L)=Vol. buffer to add (L)

OR (321.054 L)−(27.208 L)=293.846 L Buffer to add

The protein concentration was about 5.9%.

Buffer (293.846 L) was added to 27.208 L of diluted Precipitate II and mixed at a speed sufficient to create a vortex without foaming for 30 minutes.

The Viral clearance recirculation tank was charged with 107 L of diluted Ppt.II. The viral clearance recirculation tank (Pump No. 1) was started at a feed pump rate of 80% for the 20 stack Viresolve-180 module being used. The viral clearance permeate pump flow rate (Pump No. 2) was ramped to 0.91 LPM (20%) for the 20 stack module to maintain an initial transmembrane pressure (TMP) of <1.6 psi. The actual pressure maintained was 1.2 psi. The product pump rate (Pump No. 3) was adjusted to level control rate. The TMP was maintained at <3.0 psi throughout the process by monitoring the protein concentration on the retentate side of the viral clearance recirculation tank. The in-line UV monitor was observed and maintained at a range of 6.4-7.7 absorbance units to correspond to a protein content on 4.5-5.5 mg/ml.

After approximately 75 L of permeate from the viral clearance tank was charged into the ultrafiltration tank (UF), the ultrafiltration feed pump (Pump No. 5) was started at 10%. The pump speed was increased (to 25%) until the UF permeate flow rate equals the flow rate of the viral clearance permeate, then set at 25% to maintain the volume. The UF permeate flow rate was 0.91 LPM and the VC permeate flow rate was 0.91 LPM. The UF tank constant volume maintained was 152 L. The UF Feed pressure was 4.0 psi, the UF permeate pressure 0.1 psi and the UF retentate pressure 0.7 psi.

Constant volume diafiltration was performed in T-1 once the tank contained about 15-20 L. Diafiltration was maintained with a minimum of three buffer exchanges of 150 mM NaCl Glycine buffer (about 60 L total volume). The viral clearance tank pumps and mixer were turned off when the diafiltration was completed. The VC recirculation tank constant volume maintained was 15 L. The total buffer volume exchanged was 45 L.

The bulk in T-2 was recirculated and thereby concentrated by constant volume diafiltration in T-2, with the virally-cleared lot of 50 mM NaCl-Glycine buffer. The bulk was thereby concentrated to about the original starting volume of resuspended Ppt II. The permeate valve was fully open, and the UF feed pump rate was 70%; the feed pressure was maintained below 30 psi and the pressure differential maintained at 14-17 psi by applying back pressure to the retentate loop. The UF constant column maintained was 22 L and the total buffer volume exchanged was 121.2 L. A sample was drawn from T-2 to perform a digital specific conductance determination on the UF permeate sample. The result was 5.47×10−3 mhos/cm. Once the volume level was met, the UF permeate was shut off and the bulk mixed by recirculation, and a 10.5 ml sample was aseptically removed. Percent protein determination was made by refractive index using the hand held protometer on a 0.5 ml aliquot of the sample. The protein concentration was 7.9%.

The bulk from T-2 was removed into an interim bulk vessel, and the full vessel weighed (gross weight). The bulk was returned to T-2, and the empty interim bulk vessel was weighed:

Gross Weight (Kg)−Empty Vessel Weight (Kg)=Bulk Weight (Kg)

OR 58.180 (Kg)−25.24 Kg=32.94 Kg Bulk Weight

The required final volume of the bulk to achieve a 5% protein content was calculated as follows:

$$\frac{\text{Actual \% Protein} \times \text{Bulk Volume (L)}}{\text{Desired \% Protein (5.0\%)}} = \text{Required Final Vol (L)}$$

OR $$\frac{(7.9\%) \times (21.6 \text{ L})}{5.0\%} = 34.128 \text{ L Required Volume}$$

An initial pH determination was made on the remaining sample aliquot, by first diluting the aliquot 1:10 with 0.9% NaCl and titrated to a pH of 6.3-6.4 with 1:100 dilution of 0.5N HCl or 0.5N NaOH. pH was 6.55.

To adjust the pH, 1.35 mL of titrant 0.5N HCl in 0.9% NaCl was added, and the final pH was 6.35. If adjustment is required, the amount of undiluted 0.5N reagent required to adjust the pH of the bulk is calculated as follows:

$$\frac{\text{Required Final Volume (L)} \cdot \text{Volume of 1:100 titrant required (ml)}}{\text{Volume of undiluted 0.5 N reagent (ml)}}$$

OR, in this case:

34.128 L×1.35 ml=46.1 ml undiluted 0.5N reagent

Integrity testing was performed on the Viresolve-180 filter module in accordance with accepted methods. The integrity test value must be ≧1.2, and the module must be sanitized with chlorine as above and rinsed.

The bulk was adjusted to the calculated required final volume with 0.801 L of virally-cleared 50 mM NaCl-Glycine Buffer and mixed for ten (10) minutes.

A 10.5 ml aliquot of bulk product was aseptically removed for determination of pH. pH must be 6.3-6.4. Actual pH on two readings was 6.38 and 6.345.

Final protein product met the acceptance criteria as follows:

Protein=5.3%
pH=as above
Methanol content as determined by gas chromatogram was 53.9 ppm
Polysorbate 80=101.7 ppm, 102.2 ppm on two tests; average was 101.9 ppm.

Example 1A

The 150 mM NaCl-Glycine buffer employed in Example 1 was prepared as follows:
The appropriate amount of buffer to prepare was calculated as follows:

[Resuspended Paste Volume (L)×10 L]×2+60=Approx. Vol. of Buffer to prepare

[27.208 L×10 L]×2+60=604.16 L of buffer to prepare

The amount of materials required were determined and measured to a calibrated depyrogenated container:

TABLE 3

| Material | Required Conc. | × Lot Size | = Required Amount |
|---|---|---|---|
| NaCl | 8.87 g/L | 604.16 L | 5,358.90 g |
| Aminoacetic Acid | 15.01 g/L | 604.16 L | 9,068.44 g |
| Polysorbate 80 | 0.02 g/L | 604.16 L | 12.08 g |

The polysorbate weighing vessel was rinsed several times with a total of approximately 2 liters of Water for Injection, U.S.P. and each rinse aliquot was added to the batch, and qs to 604 L. The amount of the following materials were determined:

TABLE 4

| Material | Required Conc. | × Lot Size | = Required Amount |
|---|---|---|---|
| 1.0 N NaOH | 0.125 ml/L | 604.16 L | 75.52 ml |

The admixture was diluted to volume with Water for Injection, U.S.P. and the final quantity was mixed for 60 minutes. The pH was determined; requirement was 6.3-6.5, The pH was 6.38. If the requirement was not met it is necessary to add 1.0N HCl or 1.0N NaOH until the required pH is obtained; the solution should be mixed for 15-30 minutes after each addition and the pH determination confirmed.

Digital Specific Conductance Determination was performed; the requirement at 25 C is 14.15 to 15.59×10−3 mhos/cm. The result was 15.18×10−3 mhos/cm. If the requirements was not met it is necessary to discard and prepare fresh reagent.

The polysorbate 80 measurement was performed; the test sample must be 15 to 24 ppm polysorbate 80. The concentration was 19.5 ppm.

Example 2

Viral Inactivation In RhoGAM® Using S/D and Sorbent

UF Feasibility Study

Materials and Methods

Anti-D Immune Globulin

Human immunoglobulin was obtained from a full-scale modified Cohn-Oncley fractionation, (see U.S. Pat. No. 6,096,872, and Example 1 and 1A herein) followed by nano-filtration using a Viresolve 180 size-exclusion filter to produce RhoGAM® Ultra-Filtered RhO(D) Immune Globulin (Human), (Ortho-Clinical Diagnostics, Raritan, N.J.). This material was stored under sterile conditions at 2°-8° C. until use.

Viral Preparations

Viruses were prepared as titered stock cultures before spiking into the immunoglobulin. Stock cultures for bovine viral diarrhea virus (BVDV), Pseudorabies virus (PRV) and West Nile virus (WNV) (strain NIAID V-554-110-522, ATCC, Manassas, Va.) were prepared according to industry standard operating procedures.

Prior to performing the $TCID_{50}$ assay on samples collected from Ortho Clinical-Diagnostics process, plates were seeded with Vero cells. The test samples were serially diluted and inoculated at 50 μl per well into 8, 80 or 800 replicate wells. The negative control was inoculated into 8 replicate wells at 50 μl per well. The positive control, the same lot of stock virus as the spiking material, was serially diluted and each dilution was inoculated into 8 replicate wells at 50 μl per well. The observation of cultures for cytopathic effect (CPE) on day 5 post-inoculation was used to determine the virus titer. Criteria for a valid test include the negative control cultures must show the absence of viral induced CPE. The positive controls cultures must show the presence of viral induced CPE. The virus titer of the positive control must be within ±1.0 log of the certified titer of the virus.

Solvent-Detergent Sorbent

A solvent-detergent sorbent was used to remove the Triton X-100 and TNBP from some of the S/D treated samples. For each sample, a 1.0 mL aliquot of resuspended SDR HyperD Solvent-Detergent Removal Sorbent (Ciphergen Biosystems, Fremont, Calif.) was added to a 3 mL Bond Elut Reservoir (Varian Inc., Palo Alto, Calif.). The SDR HyperD was washed with 4 mL of 50 mM NaCl-Glycine buffer. 2 mL of the S/D treated sample was added to the reservoir and allowed to gravity feed through the SDR HyperD, for about 5 minutes followed by a 1.0 mL wash with 50 mM NaCl-Glycine buffer. The sample and buffer wash were collected and were assayed for virus using standard TCID50 methods. Reservoirs were discarded after use. See FIG. 1 which is a flowsheet of the S/D treatment of the IgG. The method of S/D treatment of IgG is found in Example 4.

Solvent-Detergent Treatment

S/D Stock Solution Preparation

The S/D reagents were prepared as a stock solution containing 10% detergent and 3% TNBP; one part of this stock solution was added to 9 parts of the material being treated to give a final concentration of 1% detergent and 0.3% TNBP. The stock solution was prepared by adding 10.0 g of detergent (Triton X-100) to approximately 70 mL of 50 mM NaCl-Glycine buffer (which is the buffer used in the final human immune gamma globulin (RhoGAM® or MICRhoGAM®) formulation, see U.S. Pat. No. 6,096,872 and Example 1 herein. Fairly vigorous stirring was required to dissolve the viscous detergent in the buffer. Once dissolved, 3.0 g of TNBP was added slowly over approximately 10 minutes, again with fairly vigorous stirring. The S/D stock solution was prepared and stored at room temperature, and was mixed prior to use. The solution may appear somewhat turbid due to the cloud point of the detergent.

Stock solutions of 10% Triton X-100 (Sigma Chemical Co., St. Louis, Mo.) with 3% tri-n-butyl phosphate (TNBP) (Aldrich Chemical Co. Milwaukee, Wis.) and 1% Triton X-100 with 0.3% TNBP were prepared in 50 mM NaCl-Glycine buffer, pH 6.4. Solutions were stored at 15°-30° C. until use.

Solvent-detergent treatments were performed on a 1/2000 manufacturing scale. Virus was spiked into the immune globulin at a ratio of 1:20. 20 mL aliquots of the virus-spiked immunoglobulin were equilibrated to 15° C. and solvent-detergent solution (2.0 mL) was added slowly with vigorous mixing. Seven concentrations of S/D were evaluated (and aliquots were removed at various intervals for the viral assay. See FIG. 8 for flowsheet of viral inactivation methods on virus-spiked IgG samples.

Three separate viral inactivation trials were performed, noted here as Trial 1, Trial 2 and Trial 3, with 2 or 3 runs for each Trial.

Trial 1

In Trial 1, (see FIGS. 3 & 4) BVDV and PRV were tested with the standard concentration of S/D (1.0% Triton X-100, 0.3% TNBP) and 1:10, 1:30 and 1:50 levels of the standard concentration. Virus was spiked into the load sample without Solvent/Detergent at a 1:20 dilution. The total volume of load material and virus required for the two runs were 125 ml and 6.6 ml respectively. The viral load in each case was 7 logs. Aliquots of 2.0 ml were obtained immediately after S/D addition and at 60 minutes after addition for all concentrations, and at 10, 20, 30 and 180 minutes for the 1:10 and 1:30 concentrations. During this time test samples were held at 5° C. Additionally, non-S/D treated samples were passed through a SDR HyperD column to determine whether the resin would have any effect on virus titer. All samples were immediately diluted 1:100 in buffer. See FIGS. 4 (BVDV) and 5 (PRV).

Trial 2

In Trial 2, BVDV and PRV were tested with the standard concentration of S/D and 1:10, 1:50, 1:100 and 1:200 levels of the standard concentration. Aliquots (2.0 mL) were obtained immediately after S/D addition and at 10 minutes after addition for all concentrations; at 20 minutes for the 1:50 concentration and 20 and 60 minutes for the 1:100 and 1:200 concentrations. During incubation, samples were held at 25° C. Two samples of 2.0 mL were obtained at each test interval. One sample was immediately diluted 1:100 in buffer. The second 2.0 mL aliquot was immediately passed through a SDR HyperD column. See FIG. 5 for BVDV.

Trial 3

In Trial 3, BVDV was tested at 1:10, 1:1:20 and 1:50 levels of the standard concentration of S/D. WNV was tested at the standard concentration of S/D and 1:10, 1:20, 1:50, 1:100 and 1:200 levels of the standard concentration. Aliquots of 2.0 mL were obtained immediately after S/D addition and at 10 minutes after addition for all concentrations; at 20 minutes for the 1:20 and 1:50 concentrations and at 20 and 60 minutes for the 1:100 and 1:200 concentrations. During incubation samples were held at 15° C. Two samples were obtained at each test interval. One sample was immediately diluted 1:100 in buffer. The second 2.0 mL aliquot was immediately passed through a SDR HyperD column.

Results

The initial studies with Pseudorabies Virus (PRV) and Bovine Viral Diarrhea Virus (BVDV) (see Table 5) showed that the standard concentration of S/D as well as 1:10, 1:30 and 1:50 levels of the standard S/D concentration inactivated both viruses to the limits of detection. One of the controls run in this experiment was a virus-spiked sample (not S/D treated) that was passed through a column of SDR HyperD. The data (not shown) indicated that the SDR HyperD had no effect on the titer of BVDV.

In Trial 2, BVDV was inactivated to the limits of detection with the standard and 1:10 levels of S/D. The 1:50 S/D sample showed a 4.63 log reduction, but this was not to the limit of detection. PRV was inactivated to the limit of detection by the standard S/D concentration as well as the 1:10 and 1:50 S/D level.

Trial 3 showed inactivation of BVDV to the limits of detection for the 1:20 level of S/D and a 4.69 log reduction for the 1:50 level of S/D, agreeing closely to the results from trial 2. The 1:10 level of S/D surprisingly did not show inactivation the limit of detection. WNV was inactivated to the limit of detection by the standard S/D concentration as well as the 1:10 and 1:20 S/D level. Every trial had 2 or 3 runs.

TABLE 5

Viral Inactivation Results by Virus

| Solvent/<br>Detergent<br>Concentration | Triton<br>X-100<br>(ppm) | TNBP<br>(ppm) | BVDV<br>Run 1 | BVDV<br>Run 2 | BVDV<br>Run 3 | PRV<br>Run 1 | PRV<br>Run 2 | WNV |
|---|---|---|---|---|---|---|---|---|
| Standard (1.0×) | 10,000 | 3000 | ≧4.79 ± 0.24 | ≧6.76 ± 0.28 | N/D | ≧4.60 ± 0.20 | ≧5.55 ± 0.22 | ≧4.29 ± 0.29 |
| 1:10 (0.1×) | 1000 | 300 | ≧4.79 ± 0.24 | ≧6.80 ± 0.28 | 3.28 ± 0.23 | ≧4.60 ± 0.20 | ≧5.59 ± 0.22 | ≧4.33 ± 0.29 |
| 1:20 (0.05×) | 500 | 150 | N/D | N/D | ≧5.64 ± 0.23 | N/D | N/D | ≧4.34 ± 0.29 |
| 1:30 (0.033×) | 330 | 100 | ≧4.29 ± 0.25 | N/D | N/D | ≧4.47 ± 0.25 | N/D | N/D |
| 1:50 (0.02×) | 200 | 60 | ≧4.29 ± 0.25 | 4.63 ± 0.32 | 4.69 ± 0.27 | ≧4.68 ± 0.25 | ≧5.59 ± 0.22 | 0.18 ± 0.38 |
| 1:100 (0.01×) | 100 | 30 | N/D | 4.04 ± 0.40 | N/D | N/D | 1.44 ± 0.25 | 0.75 ± 0.38 |
| 1:200 (0.005×) | 50 | 15 | N/D | 2.91 ± 0.40 | N/D | N/D | 1.67 ± 0.31 | −0.12 ± 0.41 |

BVDV, bovine viral diarrhea virus;
PRV, pseudorabies virus;
WNV, West Nile virus.
Clearance = log10(input virus ÷ output virus).

In further studies, the following final concentrations of S/D reagents outlined hereinbelow on Table 6, in RhoGAM®, were evaluated:

TABLE 6

| | Triton X-100 (ppm) | TNBP (ppm) |
|---|---|---|
| Standard Concentration (1.0×) | 10,000 | 3000 |
| 1:10 Concentration (0.10×) | 1000 | 300 |
| 1:20 Concentration (0.05×) | 500 | 150 |
| 1:50 Concentration (0.02×) | 200 | 60 |
| 1:100 Concentration (0.01×) | 100 | 30 |
| 1:200 Concentration (0.005×) | 50 | 15 |

The data from Trial 1 (see FIGS. 3 and 4, and Table 6) shows that the standard concentration of S/D as well as the 1:10 concentration was effective at inactivating both BVDV and PRV to the limits of detection within 2 minutes of addition. Additionally, with the 1:50 concentration, PRV was reduced to the limit of detection within 10 minutes, but the amount of BVDV inactivated was not as much as with the higher concentrations of S/D. In Trial 2 (see FIGS. 5 and 6 and Table 6) the BVDV run was repeated with the 1:10 and 1:50 concentrations, and a 1:20 concentration was added. This data confirms the complete inactivation at the 1:10 concentration, and also shows complete inactivation at the 1:20 concentration. As in Trial 1, the 1:50 concentration gave incomplete inactivation. The WNV data shows similar results, with the 1:10 and 1:20 concentrations giving complete inactivation within 2 minutes.

It is clear to see from the graphs of the data that in general whatever viral inactivation occurs happens within the first two minutes after addition, with no further reduction with additional exposure time to the S/D. It is thought that there is a population of virus that is essentially not affected by the S/D exposure. When a second spike is added to the S/D virus mixture the virus load is again significantly reduced without addition of more solvent/detergent. (See above Table 6)

Example 3

Column Capacity Study

Figure 8:
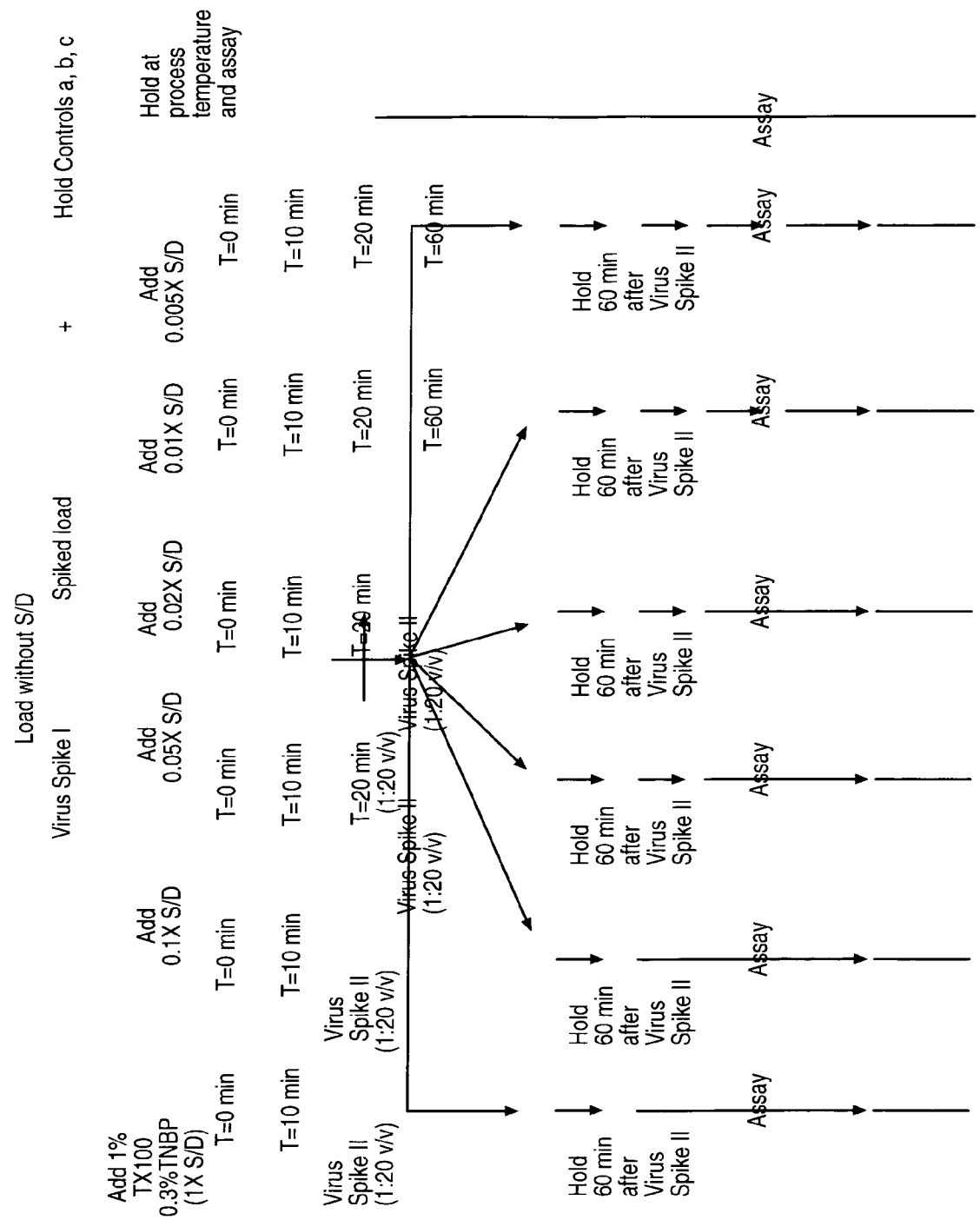
FIG. 8 is a flowsheet of the viral inactivation protocols employed in Example 2 herein.

An experiment was conducted to assess the capacity of the SDR Hyper D sorbent to remove Triton X-100 and TNBP. These results allow us to determine the approximate amount of material required for effective removal of solvent and detergent. 15 mL of 10% Triton X-100/3.0% TNBP in 50 mM NaCl/Glycine buffer was added to 135 mL of RhoGAM® bulk product (obtained by the methods of Example 4) while mixing at 22° C. The rate of addition was 1.5 mL/minute. After mixing for 1 hour, 145 mL was pumped through a preconditioned 1×10 cm column of SDR Hyper D at a flow rate of 1.0 mL/minute. Aliquots (10 mL) were collected from the column and assayed for Triton X-100 and TNBP. As shown in FIG. 8, Triton X-100 breakthrough was observed after 70 mL passed through the column. No breakthrough was seen for the TNBP indicating that the Triton X-100 concentration will be the critical parameter in calculating the amount of sorbent required.

Example 4

RhoGAM® Manufacture with S/D Treatment and Removal Using Sorbent

A pilot lot was produced that was ~⅛ the full manufacturing scale. Approximately 1.3 kg of IgG precipitate II paste was obtained from in process RhoGAM production. The paste was held at −20° C. for 2 weeks prior to resuspending in water for injection, and then diluted into high salt buffer (150 mM NaCl-glycine) containing polysorbate 80. Viresolve ultrafiltration, buffer exchange by diafiltration and bulk concentration via BioMAX 50 filter was performed prior to the solvent/detergent treatment.

The Viresolve size exclusion ultra-filtration was performed on 2-1 sq. ft standard area modules set up as instructions provided in Viresolve Virus Removal Module User Guide P36451 REV 4/02 provided by Millipore Corporation. The ultrafiltration process was run under similar conditions used during a full scale run (see Example 1) with the cross flow and the permeate flow being adjusted to take into consideration the smaller size of the membrane in the modules used. The transmembrane pressure (TMP) was held below 3 psi and comparable sieving was experienced throughout the run.

Using a Millipore Pellicon 2 Mini System with BioMAX 50K (50 kD) membranes the virally cleared Immune Globulin was concentrated to 3 to 5 liters, followed by diafiltration against 4.5 volumes of 50 mM NaCl-Glycine buffer. Three 0.1 m2 Millipore BioMAX 50 filters were used during this operation.

The treated bulk was at 21° C. prior to the start of the solvent/detergent treatment. While the bulk was mixing a 10% Triton X-100/3.0% TNBP stock solution was added by peristaltic pump to the bulk to a final concentration of 0.2% Triton X-100/0.06% TNBP. The RhoGAM bulk was mixed for one hour and then pumped through a SDR Hyper-D column to remove the solvent/detergent. Post passage through the SDR Hyper D column, the product was diafiltered threefold with 50 mM NaCl-Glycine and then concentrated to approximately 5%. This column also removes the polysorbate 80 to below 1 ppm. The polysorbate 80 was replaced in the product by pumping in a 2000 ppm stock solution over a 10 minute period.

The invention claimed is:

1. A method of virus inactivation in a post-manufacture immunoglobulin solution comprising:
    reducing the potential virus load of the immunoglobulin solution,
    adjusting the protein concentration of the immunoglobulin solution to equal or less than 6.0% w/v,
    adjusting the pH of the immunoglobulin solution to 6.3-6.4,
    contacting the immunoglobulin solution with 0.03% to 0.06% w/v of a di- or tri-alkyl phosphate solvent and 0.1% to less than 0.2% w/v of a non-ionic detergent for about 1 minute to about 1 hour at a temperature of 15-25° C.

2. The method of claim 1 wherein the immunoglobulin is anti-D immunoglobulin.

3. The method of claim 2 wherein the di- or tri-alkyl phosphate is tri-n-butyl-phosphate and the non-ionic detergent is an oxyethylated alkylphenol.

4. The method of claim 3 wherein the oxyethylated alkylphenol is a Triton®.

5. The method of claim 4 wherein the immunoglobulin solution is contacted with di- or tri-alkyl phosphate is present at 0.06% w/v and the non-ionic detergent is present at 0.2% w/v.

6. The method of claim 1 additionally comprising the step of removing the solvent and detergent from the immunoglobulin solution by a method selected from passage through a C-18 column, diafiltration through membranes, adsorption onto chromatographic supports, adsorption onto affinity chromatographic supports, ultrafiltration, filtration and adsorption, and admixture with adsorbent.

7. The method of claim 6 wherein the method is admixture with adsorbent.

8. The method of claim 7 wherein the adsorbent is a silica bead adsorbent material.

9. The method of claim 8 additionally comprising the step of removing the adsorbent from the immunoglobulin solution.

* * * * *

UNITED STATES PATENT AND TRADEMARK OFFICE
CERTIFICATE OF CORRECTION

PATENT NO. : 7,655,233 B2  Page 1 of 1
APPLICATION NO. : 11/274812
DATED : February 2, 2010
INVENTOR(S) : Van Holten et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 555 days.

Signed and Sealed this

Twenty-eighth Day of December, 2010

David J. Kappos
*Director of the United States Patent and Trademark Office*